(12) United States Patent
Keller et al.

(10) Patent No.: US 7,763,466 B2
(45) Date of Patent: Jul. 27, 2010

(54) MESODERM AND DEFINITIVE ENDODERM CELL POPULATIONS

(75) Inventors: Gordon M. Keller, New York, NY (US); Valerie Kouskoff, Manchester (GB); Atsushi Kubo, Nara (JP); Hans Joerg Fehling, Ulm (DE)

(73) Assignee: Mount Sinai School of Medicine of New York University, New York, NY (US)

( * ) Notice: Subject to any disclaimer, the term of this patent is extended or adjusted under 35 U.S.C. 154(b) by 731 days.

(21) Appl. No.: 10/514,759

(22) PCT Filed: May 19, 2003

(86) PCT No.: PCT/US03/15658

§ 371 (c)(1),
(2), (4) Date: Aug. 8, 2005

(87) PCT Pub. No.: WO2004/098490

PCT Pub. Date: Nov. 18, 2004

(65) Prior Publication Data

US 2006/0276420 A1  Dec. 7, 2006

Related U.S. Application Data

(60) Provisional application No. 60/381,617, filed on May 17, 2002, provisional application No. 60/444,851, filed on Feb. 4, 2003.

(51) Int. Cl.
  C12N 5/00  (2006.01)
  C12N 15/00  (2006.01)
(52) U.S. Cl. ...................... 435/455; 435/325
(58) Field of Classification Search .............. 435/325, 435/455
  See application file for complete search history.

(56) References Cited

U.S. PATENT DOCUMENTS

| 4,997,815 | A | * | 3/1991 | Perrine et al. ................ 514/8 |
| 5,563,059 | A | * | 10/1996 | Alak et al. ................ 800/21 |
| 6,432,673 | B1 | | 8/2002 | Gao et al. |
| 6,908,764 | B2 | | 6/2005 | Czichos et al. |
| 7,326,572 | B2 | | 2/2008 | Fisk et al. |
| 2003/0003573 | A1 | | 1/2003 | Rambhatle et al. |
| 2003/0027331 | A1 | | 2/2003 | Yan et al. |
| 2003/0109035 | A1 | | 6/2003 | Asashima et al. |
| 2004/0121464 | A1 | | 6/2004 | Rathjen et al. |
| 2005/0054102 | A1 | * | 3/2005 | Wobus et al. ............ 435/455 |

FOREIGN PATENT DOCUMENTS

| EP | 1 319 708 A2 | 6/2003 |
| WO | WO 01/53465 | 7/2001 |
| WO | WO02/29012 | 4/2002 |
| WO | WO03/083088 | 10/2003 |
| WO | WO 2005/097980 | 10/2005 |

OTHER PUBLICATIONS

Muhr et al. Assignment of early caudal identity to neural plate cells by a signal from caudal paraxial mesoderm. Neuron, vol. 19, pp. 487-502, Sep. 1997.*
Schuldiner (PNAS, Oct. 10, 2000, vol. 97, No. 21, p. 11307-11312).*
Gamer (Dev. Biol., 1995, vol. 171, p. 240-251).*
Kubo (Development and Disease, 2004, vol. 131, p. 1651-1662).*
Abe et al. (2000) Mammalian Genome 11:238-240.
Ansari-Lari et al. (1996) Genome Research 6:314-326.
Boucher et al. (2000) Int. J. Dev. Biol. 44:279-288.
Srinivas et al. (2001) BMC Developmental Biology 1:4.
Weinstein et al. (1994) Cell 78:575-588.
Keller et al. (1993) Molecular and Cellular Biology 13:473-486.
Kispert et al. (1993) The EMBO Journal 12:3211-3220.
Reyes et al. (2001) Blood 98:2615-2625.
Tada et al. (2005) Development 132:4363-4374.
Wiles et al. (1999) Experimental Cell Research 247:241-248.
Muhr et al. (1997) Neuron 19:487-502.
Rodaway et al. (2001) Cell 105:169-172.
Rodaway et al. (1999) Development 126:3067-3078.
Slager et al. (1993) Journal of Cellular Physiology 156:247-256.
Takahashi et al. (1998) Protein, Nucleic Acid and enzyme 43:1347-1354.
Wilson et al. (1993) Development 117:1321-1331.
Rashbass et al. Nature 353:348-351, Sep. 26, 1991.
Conquet. Neuropharmacology 34(8):865-870, 1995.
Mao et al. Blood 97:324-326, 2001.
Yasunaga et al. (2005) Induction and Monitoring of Definitive and Visceral Endoderm Differentiation of Mouse ES Cells, 23:1542-1550.
Abe et al. (1996) Experimental Cell Research 229:27-34.
Kubo et al. (2004) Development 131:1651-1662.
Lagasse et al. (2000) Nature Medicine 6:1229-1234.
Asashima et al., Transplantation Now, 2000, 13: 330-336.
Edwards et al., Genome Res., 1996, 6: 226-233.
Eiges et al., Current Biol., 2001, 11: 514-518.
Guan et al., Cytotechnology, 1996, 30: 211-226.
Hamazaki et al., FEBS Lett., 2001, 497: 15-19.
Kimelman et al., Curr.Opin.Genetics Dev., 2000, 10: 350-356.
Davis et al., Blood, 2008, 111: 1876-1884.
Hockemeyer et al., Nature Biotechnology, 2009, 27: 851-858.
Urbach et al., Stem Cells, 2004, 22: 635-641.
Zou et al., Cell Stem Cell, 2009, 5: 97-110.
Zwaka et al., Nature Biotechnology, 2008, 21: 319-321.

* cited by examiner

*Primary Examiner*—Michael C. Wilson
(74) *Attorney, Agent, or Firm*—Crowell & Moring LLP

(57) ABSTRACT

The present invention provides cell populations that are enriched for mesendoderm and mesoderm, and cell populations that are enriched for endoderm. The cell populations of the invention are useful for generating cells for cell replacement therapy.

7 Claims, 31 Drawing Sheets

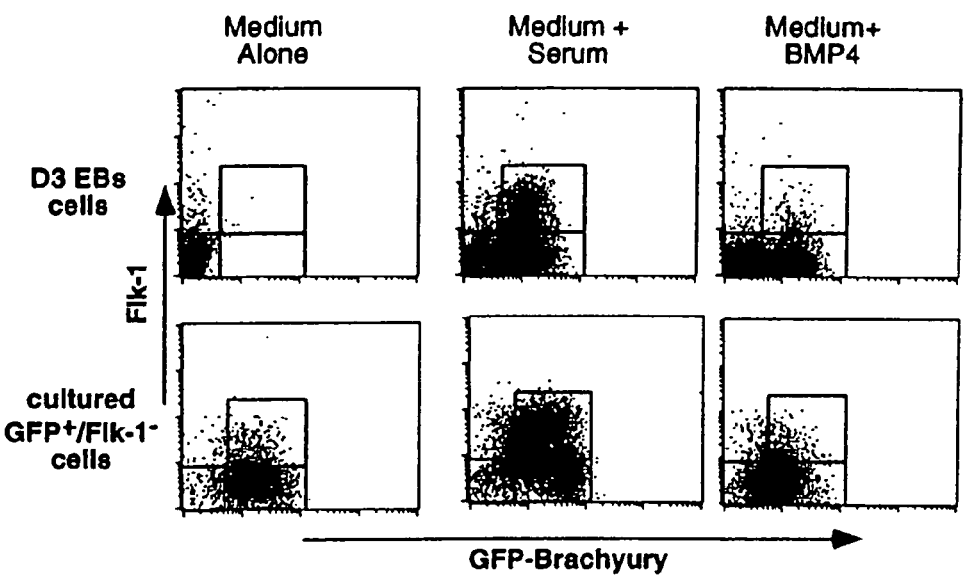

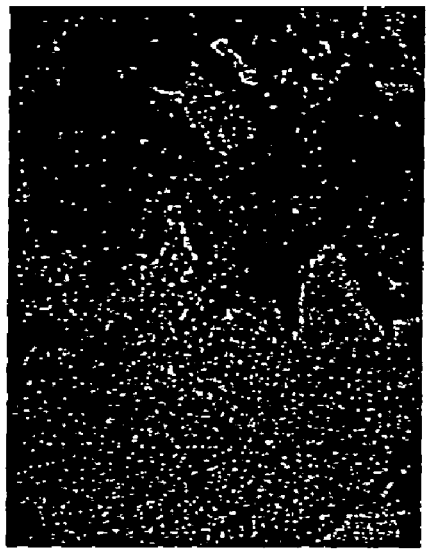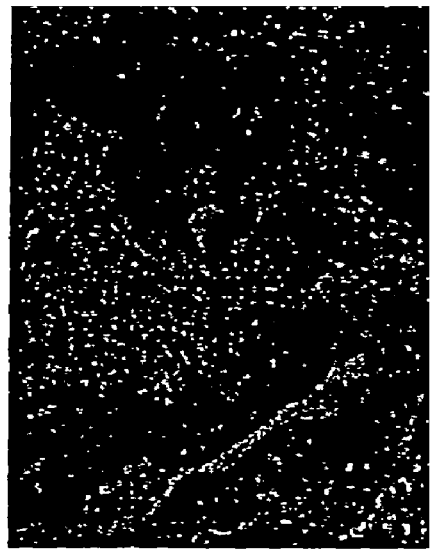
Fig. 26C

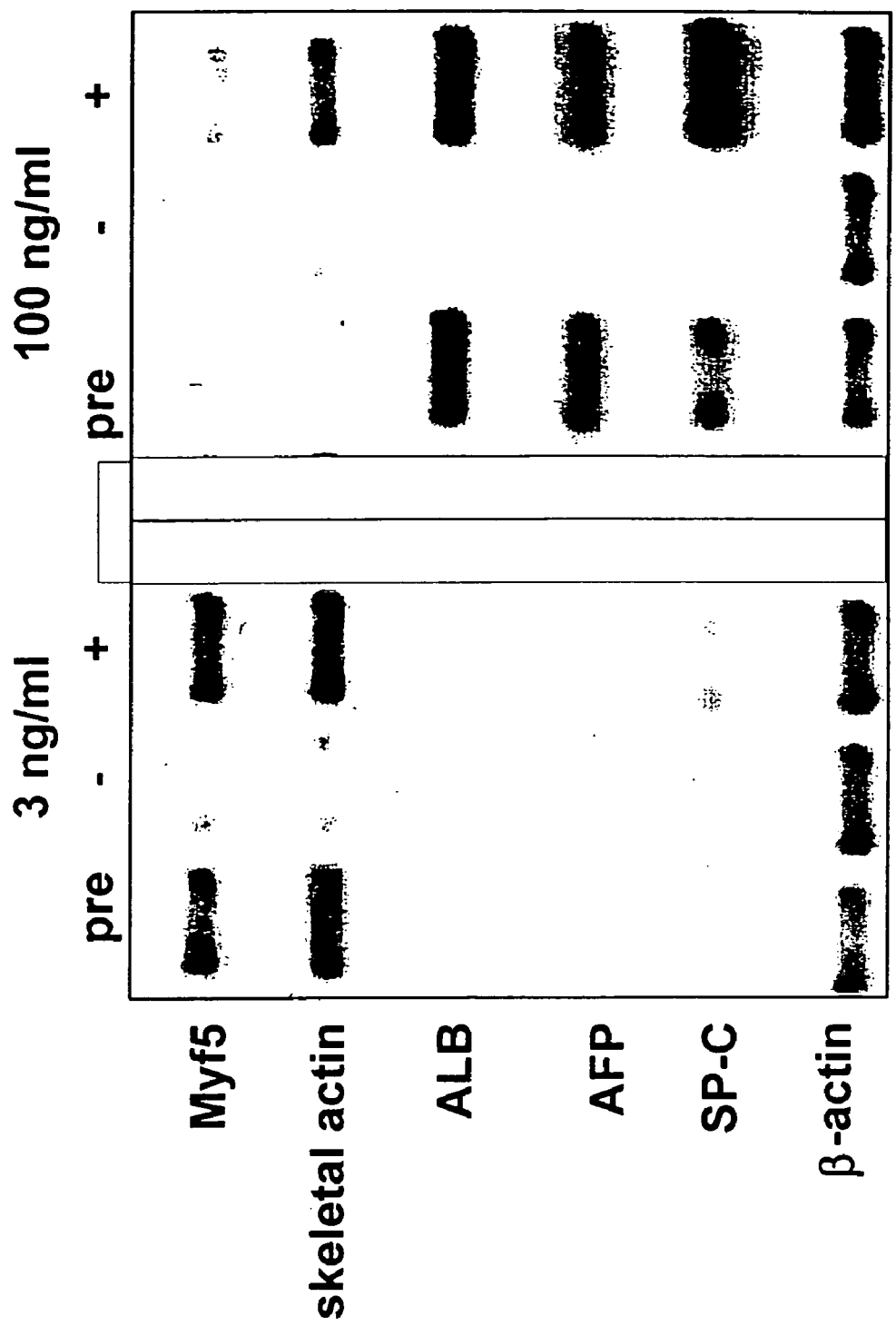

SEQUENCE LISTING

<160> NUMBER OF SEQ ID NOS: 15

<210> SEQ ID NO 1
<211> LENGTH: 40
<212> TYPE: DNA
<213> ORGANISM: Artificial
<220> FEATURE:
<223> OTHER INFORMATION: Synthetic

<400> SEQUENCE: 1
gttaactcga gaattctttt tttttttttt tttttttttt                         40

<210> SEQ ID NO 2
<211> LENGTH: 32
<212> TYPE: DNA
<213> ORGANISM: Artificial
<220> FEATURE:
<223> OTHER INFORMATION: Synthetic

<400> SEQUENCE: 2
tggagtcaaa gagggcatca tagacacatg gg                                 32

<210> SEQ ID NO 3
<211> LENGTH: 24
<212> TYPE: DNA
<213> ORGANISM: Artificial
<220> FEATURE:
<223> OTHER INFORMATION: Synthetic

<400> SEQUENCE: 3
cagtacactg gccaatccca tgtg                                          24

<210> SEQ ID NO 4
<211> LENGTH: 23
<212> TYPE: DNA
<213> ORGANISM: Mus musculus

<400> SEQUENCE: 4
aaggagctaa ctaacgagat gat                                           23

<210> SEQ ID NO 5
<211> LENGTH: 21
<212> TYPE: DNA
<213> ORGANISM: Mus musculus

<400> SEQUENCE: 5
taccttcagc accgggaaca t                                             21

<210> SEQ ID NO 6
<211> LENGTH: 17
<212> TYPE: DNA
<213> ORGANISM: Artificial
<220> FEATURE:
<223> OTHER INFORMATION: Synthetic

<400> SEQUENCE: 6
gctagctaat ggatcca                                                    17

<210> SEQ ID NO 7
<211> LENGTH: 25
<212> TYPE: DNA
<213> ORGANISM: Artificial
<220> FEATURE:
<223> OTHER INFORMATION: Synthetic

<400> SEQUENCE: 7
gatctggatc cattagctag ctgca                                           25

<210> SEQ ID NO 8
<211> LENGTH: 36
<212> TYPE: DNA
<213> ORGANISM: Artificial
<220> FEATURE:
<223> OTHER INFORMATION: Synthetic

<400> SEQUENCE: 8
gatcttaatg aacggcaggt gggtgcgcgt ccggag                               36

<210> SEQ ID NO 9
<211> LENGTH: 36
<212> TYPE: DNA
<213> ORGANISM: Artificial
<220> FEATURE:
<223> OTHER INFORMATION: Synthetic

<400> SEQUENCE: 9
tcgactccgg acgcgcaccc acctgccgtt cattaa                               36

<210> SEQ ID NO 10
<211> LENGTH: 21
<212> TYPE: DNA
<213> ORGANISM: Artificial
<220> FEATURE:
<223> OTHER INFORMATION: Synthetic

<400> SEQUENCE: 10
cgcgttacta gtaagacgtc t                                               21

<210> SEQ ID NO 11
<211> LENGTH: 21
<212> TYPE: DNA
<213> ORGANISM: Artificial
<220> FEATURE:
<223> OTHER INFORMATION: Synthetic

<400> SEQUENCE: 11
ccggagacgt cttactagta a                                               21

<210> SEQ ID NO 12
<211> LENGTH: 23
<212> TYPE: DNA
<213> ORGANISM: Artificial
<220> FEATURE:
<223> OTHER INFORMATION: Synthetic

```
<400> SEQUENCE: 12
caggtagaac ccacaactcc gac                                                23

<210> SEQ ID NO 13
<211> LENGTH: 22
<212> TYPE: DNA
<213> ORGANISM: Artificial
<220> FEATURE:
<223> OTHER INFORMATION: Synthetic

<400> SEQUENCE: 13
ccggacacgc tgaacttgtg gc                                                 22

<210> SEQ ID NO 14
<211> LENGTH: 30
<212> TYPE: DNA
<213> ORGANISM: Artificial
<220> FEATURE:
<223> OTHER INFORMATION: Synthetic

<400> SEQUENCE: 14
acaggatccc taagcctcaa aagagtcgct                                         30

<210> SEQ ID NO 15
<211> LENGTH: 33
<212> TYPE: DNA
<213> ORGANISM: Artificial
<220> FEATURE:
<223> OTHER INFORMATION: Synthetic

<400> SEQUENCE: 15
tcttggatcc tcctatccta tcccgaagct cct                                     33
```

MESODERM AND DEFINITIVE ENDODERM CELL POPULATIONS

CROSS-REFERENCE TO RELATED APPLICATION

This application claims the benefit of U.S. Application Ser. Nos. 60/381,617 filed May 17, 2002 and 60/444,851 filed Feb. 4, 2003, the disclosures of which are incorporated herein by reference.

STATEMENT REGARDING FEDERALLY SPONSORED RESEARCH

This invention was made with government support under Grant Nos. 2RO1 HL 48834-09 and 2RO1 HL 65169-02 awarded by the National Institutes of Health. The government may have certain rights in the invention.

BACKGROUND OF THE INVENTION

During embryonic development, the tissues of the body are formed from three major cell populations: ectoderm, mesoderm and definitive endoderm. These cell populations, also known as primary germ cell layers, are formed through a process known as gastrulation. Following gastrulation, each primary germ cell layer generates a specific set of cell populations and tissues. Mesoderm gives rise to blood cells, endothelial cells, cardiac and skeletal muscle, and adipocytes. Definitive endoderm generates liver, pancreas and lung. Ectoderm gives rise to the nervous system, skin and adrenal tissues.

The process of tissue development from these germ cell layers involves multiple differentiation steps, reflecting complex molecular changes. With respect to mesoderm and its derivatives, three distinct stages have been defined. The first is the induction of mesoderm from cells within a structure known as the epiblast. The newly formed mesoderm, also known as nascent mesoderm, migrates to different positions that will be sites of future tissue development in the early embryo. This process, known as patterning, entails some molecular changes that are likely reflective of the initial stages of differentiation towards specific tissues. The final stage, known as specification, involves the generation of distinct tissues from the patterned mesodermal subpopulations. Recent studies have provided evidence which suggests that mesoderm is induced in successive waves which represent subpopulations with distinct developmental potential. The mesoderm that is formed first migrates to the extraembryonic region and gives rise to hematopoietic and endothelial cells, whereas the next population migrates anteriorly in the developing embryo and contributes to the heart and cranial mesenchyme. These lineage relationships were defined initially through histological analysis and have been largely confirmed by cell tracing studies. While this segregation of developmental fates is well accepted in the field of developmental biology, to date, there are no available methods of isolating mesoderm and endoderm, prior to commitment to these lineages.

The present invention provides a method for isolating mesoderm and definitive endoderm cell populations. These cell populations are useful to identify agents that affect cell growth and differentiation, to identify genes involved in tissue development, and to generate differentiated cells and tissues for cell replacement therapies.

SUMMARY OF THE INVENTION

The present invention provides cell populations that are enriched for mesendoderm and mesoderm cells. Mesendoderm cells are defined herein as cells that express brachyury (brach$^+$) and which, in the presence of differentiation-inducing conditions, are capable of generating mesoderm and mesoderm derivatives including cardiac and skeletal muscle, vascular smooth muscle, endothelium and hematopoietic cells, and also are capable of generating endoderm and endoderm derivatives including liver cells and pancreatic cells. Mesoderm cells are defined herein as cells that are brach$^+$ and which, in the presence of differentiation inducing conditions, are capable of generating cardiac and skeletal muscle, vascular smooth muscle, endothelium and hematopoietic cells, and are not capable of generating endoderm and endoderm derivatives.

The present invention further provides cell populations that are enriched for endoderm cells. Endoderm cells are defined herein as cells that do not express brachyury (brach$^-$) and which, in the presence of differentiation-inducing conditions, are capable of generating lung cells, liver cells and pancreatic cells.

The present invention also provides methods of isolating cell populations enriched for mesendoderm and mesoderm cells, and cell populations enriched for endoderm cells. In another embodiment, the present invention provides methods of identifying agents that affect the proliferation, differentiation or survival of the cell populations of the invention. A method of identifying genes involved in cell differentiation and development of specific lineages and tissues is also provided.

Antibodies that specifically recognize brach$^+$ cells are also provided. The antibodies are useful, for example, for isolating mesendoderm and mesoderm cell populations.

In another embodiment, the present invention provides a method for generating cells in vitro. Such cells are useful, for example, for cell replacement therapy.

The present invention also provides a transgenic non-human mammal having a genome in which DNA encoding a selectable marker is present in the brachyury locus such that one brachyury allele is inactivated and the selectable marker is expressed in cells in which the brachyury locus is transcribed.

BRIEF DESCRIPTION OF THE DRAWINGS

FIG. 2A depicts the kinetics of brachyury expression determined by reverse transcriptase-polymerase chain reaction (RT-PCR). FIG. 2B depicts the kinetics of GFP expression determined by fluorescence activated cell sorting (FACS) analysis. Numbers above the figure in FIG. 2A and the histograms in FIG. 2B represent day of EB differentiation.

FIG. 3A is a histogram showing developmental potential of day 6 EBs. (Mac/Ery: colonies of macrophages and definitive erythroid cells; Mac: pure macrophage colonies; Ery$^d$: colonies of definitive erythroid cells; Mix: multilineage colonies; Ery$^p$: primitive erythroid colonies. FIG. 3B is a histogram depicting blast colony-forming cell (BL-CFC) potential of EBs. FIG. 3C shows gene expression patterns during EB development for wild-type and GFP-Bry cells. Numbers at the top of the lanes represent day of EB differentiation.

FIG. 4A shows the profile of GFP expression in day 3.5 EBs. 1 and 2 represent the gates used to isolate the GFP$^-$ and GFP$^+$ fractions. FIG. 4B depicts RT-PCR expression analysis of isolated fractions.

FIG. 5A depicts the profiles and gates used to isolate the GFP$^-$/Flk-1$^-$, GFP$^+$/Flk-1$^-$ and GFP$^+$/Flk-1$^+$ fractions from day 3.0 and 3.5 EBs Numbers next to the gates represent the three different populations. FIG. 5B shows the Blast colony (Blast) and secondary EB (2°) potential of the different fractions. FIG. 5C shows the expression analysis of the isolated fractions. Expression shown in the top panel was evaluated using a polyA$^+$ global amplification PCR method described by Brady et al. (1990) Meth. In Mol. And Cell Bio. 2:17-25. The data in the lower panels was obtained by RT-PCR analysis using gene specific oligonucleotides. Numbers on the top of each row indicate the cell population as designated in FIG. 5A.

In FIG. 7A, the numbers on the bottom refer to the cell population: 1 is the presort, 3 is the GFP$^+$/Flk-1$^-$ fraction and 4 is the GFP$^+$/Flk-1$^+$ fraction. Cells were cultured for 20 hours, and the aggregates were then dissociated and analyzed for BL-CFC. Data are shown for cells isolated from day 3, 3.5 and 4.0 EBs. In FIG. 7B, the top row represents GFP$^+$/Flk-1$^-$ cells isolated from day 3.0, 3.5 and 4.0 EBs prior to culture (pre). The bottom row shows the Flk-1 expression pattern of the same fraction, following culture (post). Numbers above the bars represent the percentage of Flk-1$^+$ cells.

FIGS. 8A and 8B demonstrate the effects of BMP-4 and fetal calf serum (FCS) on the development of brachyury and Flk-1$^+$ in/on day 3.0 EB derived cells under the conditions indicated at the top of each histogram. FIG. 8B depicts expression of brachyury and Flk-1 on cell populations generated from GFP$^+$//Flk-1$^-$ cells cultured for 20 hours under the indicated conditions.

FIG. 29 depicts expression analysis of brachyury fractions isolated from activin-induced populations. Numbers at the top of the figure indicate activin concentration.

DETAILED DESCRIPTION OF THE INVENTION

Figure 1:
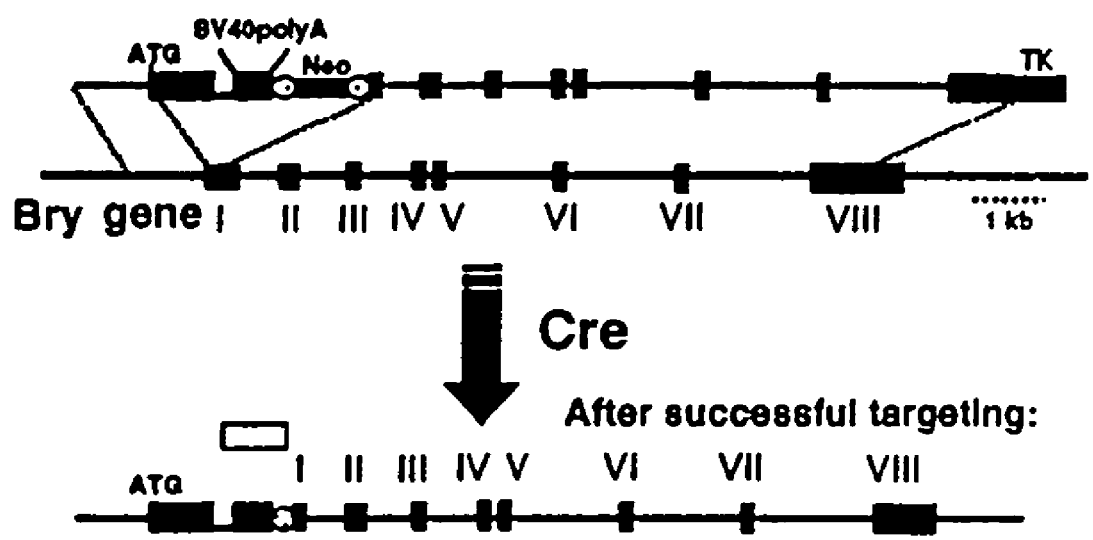
FIG. 1 depicts the scheme of the vector and the strategy used for targeting the green fluorescence protein (GFP) to the brachyury locus.

During embryogenesis, the formation of mesoderm is a critical step in the establishment of a body plan and in the development of multiple organ systems such as blood, endothelium, heart and skeletal muscle. The molecular mechanisms that control mesoderm formation, however, are poorly defined. A model system based upon the differentiation of embryonic stem (ES) cells in culture has been used to study mesodermal-derived populations including hematopoietic, endothelial, cardiac and skeletal muscle and adipocyte lineages. The in vitro model supports the induction and specification of mesoderm, but these differentiation events take place in complex colonies known as embryoid bodies (EBs) generated from ES cells. It would be advantageous to isolate mesoderm cell populations from EBs as they are formed, in order to better understand mesoderm formation and tissue development. However, it has not been possible to isolate these populations by cell sorting using antibodies, because antibodies specific for nascent mesoderm cell populations are not well-defined.

Brachyury (also known as T) is the founding member of a family of transcription factors known as T-box genes and was first identified as a naturally occurring mutation in mice. Papaioannou et al. (1998) Bioessays 20:9-19. Heterozygous mice are viable but have a shorter tail than wild type animals. Homozygous mutants, which die at approximately day 10 p.c., lack a notochord and display defects in the development of posterior mesodermal tissues. Through the analysis of chimeric animals, brachyury has been shown to affect the migratory properties of the mesodermal cells. Wilson et al. (1995) Development 121:877-86. Expression analysis revealed a unique and interesting pattern for brachyury. It is expressed transiently in all cells ingressing through the primitive streak as well as in the nascent and early migrating mesoderm. Wilkinson et al. (1990) Nature 343:657-9; Herrmann et al. (1991) Development 113:913-7. Expression is rapidly downregulated in paraxial, lateral and extraembryonic mesoderm and following regression of the steak, is confined to the tailbud and notochord. Given this pattern, brachyury is considered to be one of the best markers of early mesoderm and is used to track the development of this lineage. Brachyury has been identified in all species analyzed, suggesting that its role in mesoderm development is preserved throughout phylogeny. Papaioannou et al. (1998).

In accordance with the present invention, a selectable marker gene has been recombinantly targeted to the brachyury locus. It has been discovered that, following the initiation of ES cell differentiation, the selectable marker is expressed in a pattern that reflects brachyury expression. The selectable marker has allowed the sorting of brachyury positive (Brach$^+$) cells from EBs, and thereby the isolation and characterization of cell populations that are enriched for mesendoderm and mesoderm cells.

The selectable marker exemplified in accordance with the present invention is the enhanced green fluorescence protein (EGFP or GFP). Other selectable markers that will facilitate cell sorting are known to those of ordinary skill in the art and may be used in the present invention. The cDNA encoding GFP is known in the art (and is commercially available, for example as plasmid pEGFP.C1 from Clontech, Palo Alto, Calif.), and may be targeted to the brachyury locus by constructing targeting vectors (GFP-Bry) by methods known in the art. The vectors are preferably designed to replace approximately two-thirds of the first exon of the brachyury gene with a GFP expression cassette.

Brachyury genes from numerous species, including human and mouse, are known in the art and reviewed, for example, by Smith (1997) Current Opinion in Genetics & Development 7:474-480. The GFP expression cassette preferably contains GFP cDNA and one or more translational stop codons to prevent translation of downstream brachyury exons. The cassette may further contain an exon encoding the SV40 polyadenylation signal sequence to prevent transcription of downstream regions of the brachyury gene.

The vectors are introduced into ES cells by methods known in the art to integrate the GFP-Bry construct by homologous recombination. ES cells may be isolated from blastocysts by methods known in the art and disclosed for example by Evans et al. (1981) Nature 292:154-156, Thomson et al. (1995) Proc. Nat'l. Acad. Sci. USA 92; 7844; U.S. Pat. No. 5,843,780; and Reubinoff et al. (2000) Nature Biotech. 18:399. In a preferred embodiment the ES cells are mouse or human ES cells. Following successful targeting the brachyury start codon becomes the start codon of GFP, resulting in the disruption of the targeted brachyury allele. The resulting cells are designated GFP-Bry ES cells. GFP-Bry ES cells are defined herein as ES cells in which one brachyury allele is inactivated and GFP is expressed under the control of the brachyury regulatory elements.

It has been discovered in accordance with the present invention that GFP-Bry ES cells, in which one brachyury allele is inactivated, are viable and develop and differentiate normally. Further, it has been discovered that GFP expression mirrors endogenous brachyury expression. Accordingly, brach$^+$ cells may be isolated by selecting for cells that express GFP. Cells that express GFP may conveniently be isolated by flow cytometry, for example by fluorescence-activated cell sorting (FACS). Methods for sorting cells based on fluorescent properties are well-known to those of ordinary skill in the art.

Cell populations that are enriched for mesendoderm and mesoderm cells, as defined hereinabove, may be obtained by culturing GFP-Bry ES cells in the presence of serum for a time sufficient to obtain GFP$^+$ cells, for example for from about one to about four days for mouse cells, and sorting and isolating GFP$^+$ cells, for example by flow cytometry. The cell population that is isolated contains at least about 50%, and preferably at least about 75%, and more preferably at least about 90%, and most preferably at least about 95% or at least about 99% mesendoderm and mesoderm cells. The relative amounts of mesendoderm and mesoderm may be varied by adjusting the length of the culture in serum, with shorter culture times favoring the presence of mesendoderm and mesoderm patterned to the hematopoietic and endothelial lineages, and longer culture times favoring the presence of mesoderm patterned to the cardiac and skeletal muscle lineages. For example, a cell population enriched for mesoderm may be obtained by culturing in serum for about 2.5 to 4.5 days, followed by sorting and isolating GFP$^+$ cells. Culturing in the presence of serum is defined herein as culturing in media supplemented with animal serum, for example fetal calf serum (FCS). In a preferred embodiment, the media is supplemented with from about 5% to about 25% serum. The optimal concentration may be serum batch dependent and can be determined by one of ordinary skill in the art.

Cell populations that are enriched for mesendoderm and mesoderm cells may be obtained from GFP-Bry ES cells generated from human ES cells by a similar method in which the length of time of culture in serum is lengthened to account for difference in times of differentiation in vitro for human and mouse cells. Accordingly, GFP-Bry ES cells generated from human ES cells are cultured in serum for a time sufficient to obtain GFP$^+$ cells, for example about 2 to about 18 days, before sorting and isolating GFP$^+$ cells.

For both mouse and human cell populations, it can be easily determined whether the isolated cells have differentiated beyond mesoderm, for example to hemangioblasts, by assaying for the presence of the tyrosine kinase receptor, human KDR or mouse Flk-1. KDR and Flk-1 are not expressed in mesendoderm and nascent mesoderm, but as these cells differentiate to a hemangioblast/pre-erythroid population, KDR or Flk-1 expression is detectable. KDR$^+$ and flk-1$^+$ cells may be identified by flow cytometry using antibodies to KDR or Flk-1. Such antibodies are known in the art, and may also be generated using standard methods of antibody production. The cell populations enriched for mesendoderm and mesoderm may be further enriched by removing KDR$^+$ or Flk-1+cells by cell sorting.

Figure 17:
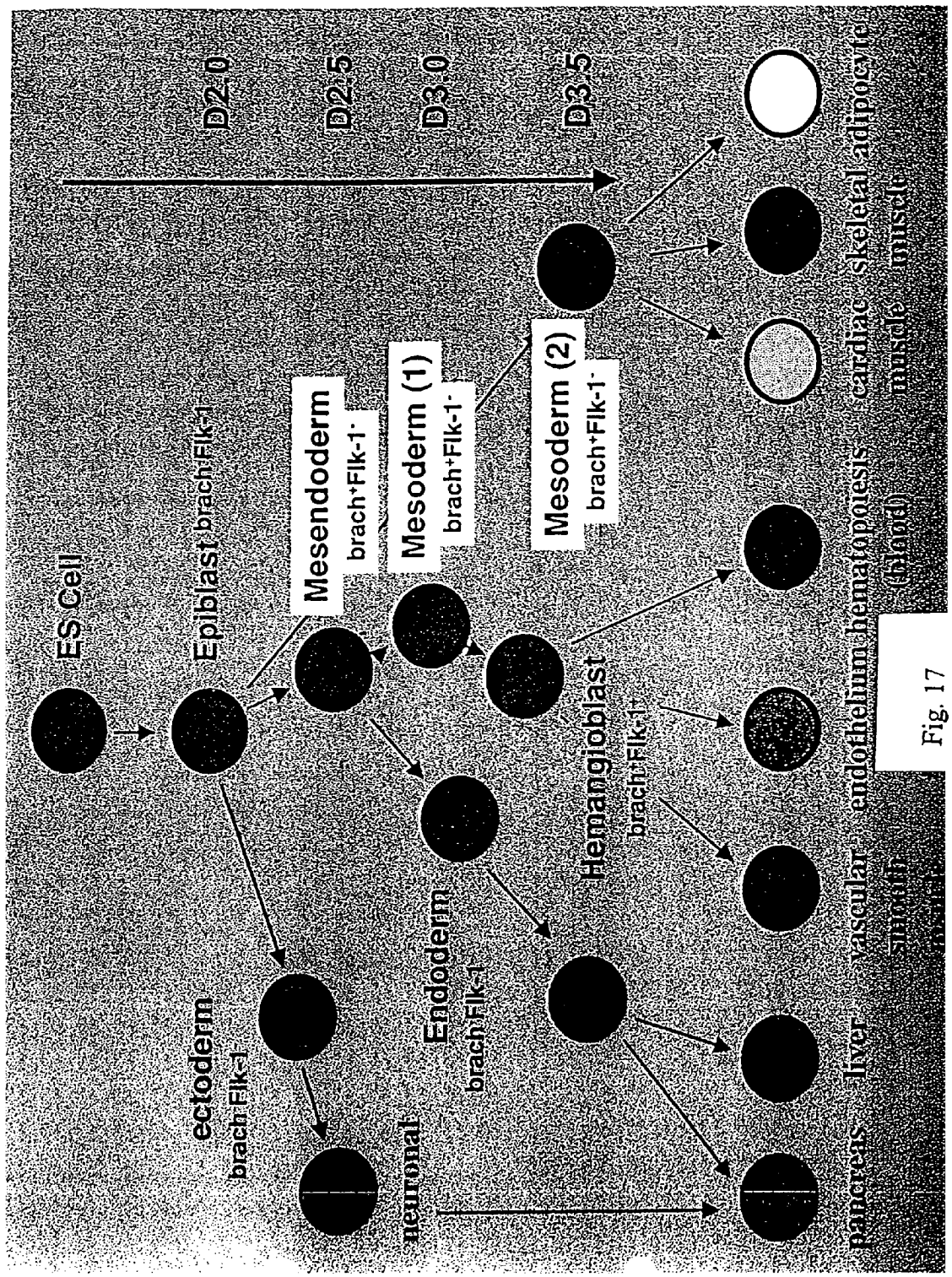
FIG. 17 is a diagram of the mesoderm and endoderm populations of the present invention and the differentiation of these population to derivative cell types.

As depicted in FIG. 17, it has been discovered in accordance with the present invention that mesendoderm is a previously unidentified cell population that gives rise to both endoderm and mesoderm and their corresponding lineages. It has been further discovered that presence or absence of serum in the in vitro culture may be used to dictate which lineage is generated from mesendoderm. In particular, a cell population that is enriched for endoderm cells may be obtained by culturing GFP-Bry ES cells generated from mouse ES cells in the presence of serum for about two to four days, sorting and isolating GFP$^+$ cells, for example by flow cytometry, followed by culturing the GFP in the absence of serum for from about one to about ten days. The cell population that is isolated contains at least 50%, and preferably at least about 75%, and more preferably at least about 90%, and most preferably at least about 95% or at least about 99% endoderm cells, as defined hereinabove.

Cell populations that are enriched for endoderm cells may be obtained from GFP-Bry ES cells generated from human ES cells by culturing the GFP-Bry ES cells in the presence of serum for about 2 to 10 days, and then sorting and isolating GFP$^+$ cells followed by culturing the GFP$^+$ cells in the absence of serum for from about 1 to about 15 days.

The populations enriched for endoderm cells may be further enriched by identifying and sorting out KDR$^+$ or Flk-1$^+$ cells as described above.

It has further been discovered in accordance with the present invention that cell populations enriched for endoderm may be obtained by culturing GFP-Bry embryonic stem cells in the absence of serum and in the presence of the growth factor activin, for about two to about ten days, and isolating cells that express brachyury. The amount of activin is sufficient to induce differentiation of embryonic stem cells to endoderm. Such differentiation may be measured by assaying for the expression of genes associated with endoderm development, including for example HNF3β, Mixl-1, Sox17, Hex-1 or pdx-1. In a preferred embodiment, the concentration of activin is at least about 30 ng/ml. In another preferred embodiment the concentration of activin is about 100 ng/ml.

Cell populations enriched for mesoderm may be obtained by culturing GFP-Bry embryonic stem cells in the absence of serum and the presence of activin for about two to about ten days, and isolating cells that express brachyury. The amount of activin is sufficient to induce differentiation of embryonic stem cells to mesoderm, but insufficient to induce differentiation to endoderm. Differentiation to mesoderm may be measured by assaying for the expression of genes associated with mesoderm development, including for example GATA-1, and the absence of expression of genes associated with endoderm development. In a preferred embodiment, the concentration of activin is less than 30 ng/ml. In another preferred embodiment the concentration of activin is about 3 ng/ml.

The present invention further provides a method of identifying agents that affect the proliferation, differentiation or survival of the cell populations described above. The method comprises culturing cells from one of the cell populations described hereinabove in the absence and presence of an agent to be tested, and determining whether the agent has an effect on proliferation, differentiation or survival of the cell population. The agent to be tested may be natural or synthetic, one compound or a mixture, a small molecule or polymer including polypeptides, polysaccharides, polynucleutides and the like, an antibody or fragment thereof, a compound from a library of natural or synthetic compounds, a compound obtained from rational drug design, or any agent the effect of which on the cell population may be assessed using assays known in the art, for example standard proliferation and differentiation assays as described in U.S. Pat. No. 6,110,739. Such agents are useful for the control of cell growth and differentiation in vivo and in vitro.

The present invention further provides a method of identifying genes involved in cell differentiation and development of specific lineages and tissues. The method comprises isolating populations of GFP$^+$ cells of the invention after different amounts of time in culture, comparing gene expression profiles in the different populations, and identifying genes that are uniquely expressed in a population. In a preferred embodiment, microarray analysis and subtractive hybridization are used to compare gene expression profiles.

In another embodiment, the present invention provides methods of making antibodies that recognize brachyury positive (brach$^+$) cells but not brachyury negative (brach$^-$) cells. Polyclonal antibodies may be made by injecting an animal with the cells of the invention in an immunogenic form. Also, antibodies may be made by identifying cells surface markers present in GFP$^+$ but not GFP$^-$ cells, and making antibodies against the markers or fragments thereof. The antibodies may be monoclonal or polyclonal, and may be fragments, genetically engineered antibodies, single chain antibodies, and so on. Antibodies may be made by methods well-known in the art. Such antibodies are useful for identifying and isolating brach$^+$ cells such as mesendoderm and mesoderm.

The present invention also provides a method for generating mammalian cells in vitro. In one embodiment, the method comprises culturing cells from a cell population enriched in mesendoderm and mesoderm cells under conditions effective for the differentiation of mesoderm into cardiac muscle, vascular smooth muscle, endothelium or hematopoietic cells. Conditions effective for differentiation into the various cell types in vitro are known in the art. In another embodiment, the method comprises culturing cells from a cell population enriched in endoderm cells under conditions effective for the differentiation of endoderm into liver cells or pancreatic cells. Effective conditions for such differentiation are known in the art. The production of insulin-producing pancreatic islet cells is specifically contemplated.

As demonstrated in accordance with the present invention, brach$^+$ cells isolated from different aged EBs have different developmental potentials. Brach$^+$/Flk$^-$ cells from about day 3 mouse EBs efficiently generate hemotopoietic and endothelial lineages, while the cells from about day 3 to 10 EBs generate cells of cardiomyocyte lineages. Accordingly, by adjusting the time of culture of the ES cells used for obtaining the cell population enriched for mesendoderm and mesoderm, one of ordinary skill in the art can select for efficient production of hemotopoetic and endothelial lineages or cardiomyocyte lineages.

Such cells are useful, for example, for cell replacement therapy for the treatment of disorders that result from destruction or dysfunction of a limited number of cell types. Such disorders include diabetes mellitus, liver failure, heart failure, cardiovascular and other vascular disease, Duchenne's muscular dystrophy, osteogenesis imperfecta, and disorders treatable by bone marrow transplant, for example leukemias and anemias. See, Odorico et al., (2001) Stem Cells 19:193-204.

The cell populations of the present invention are useful for generating differentiated cells and tissues for cell replacement therapies. The suitability of the cell populations of the present invention for cell replacement therapy may be assessed by transplanting the cells into animal models of disorders that are associated with the destruction or dysfunction of a limited number of cell types. For example, the fumarylacetoacetate (FAH) deficient mouse disclosed for example by Grompe et al. (1993) *Genes & Dev.* 7:2298, incorporated herein by reference, provides a model for liver failure. FAH deficient mice suffer from progressive liver failure and renal tubular damage unless treated with NTBC (2-(2-nitro-4-trifluoromethyl benzoyl)-1,3-cyclohexedione) or transplanted with normal hepatocytes. These mice thus provide an ideal model for testing the potential of cells with characteristics of immature hepatocytes generated from EBs. Methods for transplantation of hepatocytes into FAH deficient mice removed from NTBC are known in the art and disclosed for example by Oversturf et al. (1996) *Nature Genet.* 12:266-273. Normal liver function is indicated by survival of the mice, and may also be assessed by measuring serum aspartate transaminase levels, plasma bilirubin levels, and by determining normal structure of the regenerated liver.

Animal models for other disorders that result from the destruction or dysfunction of particular cells types are known in the art. Such models may similarly be used to assess other cell populations of the present invention.

The present invention also provides a transgenic non-human mammal in which DNA encoding a selectable marker is present in the brachyury locus such that one brachyury allele is inactivated and the selectable marker is expressed in cells in which the brachyury locus is transcribed. In a preferred embodiment the mammal is a mouse and the selectable marker is GFP. In particular, the transgenic mouse has a genome comprising a transgene in which a DNA sequence encoding GFP is operably linked to brachyury regulatory elements, and the transgene is expressed in cells that normally express brachyury. The transgenic mouse may be obtained by injecting the GFP-Bry ES cells described hereinabove into blastocysts, which are then implanted into pseudopregnant females. Transgenic pups are identified by the short-tail phenotype associated with brach +/−, and by molecular analysis. Such transgenic animals are useful for obtaining early embryos from which to isolate mesoderm to be used in accordance with the methods of the invention, and for the identification, isolation and characterization of any adult cell populations that express the brachyury gene. Such cells may represent novel stem cell populations.

All references cited herein are incorporated herein in their entirety.

The following examples serve to further illustrate the present invention.

EXAMPLE 1

Materials and Methods

ES cell growth and differentiation. ES cells were maintained on irradiated embryonic feeder cells in Dulbecco's Modified Eagle Medium (DMEM) supplemented with 15% fetal calf serum (FCS), penicillin, streptomycin, LIF (1% conditioned medium) and $1.5 \times 10^{-4}$ M monothioglycerol (MFG; Sigma). Two days prior to the onset of differentiation, cells were transferred on gelatinized plates in the same media. For the generation of EBs, ES cells were trypsinized and plated at various densities in differentiation cultures. Differentiation of EBs was carried out in 60 mm petri grade dishes in IMDM supplemented with 15% FCS, 2 mM L-glutamine (Gibco/BRL), transferrin (200 ug/ml), 0.5 mM ascorbic acid (Sigma), and $4.5 \times 10^{-4}$ M MTG. Cultures were maintained in a humidified chamber in a 5% $CO_2$/air mixture at 37° C.

Serum Free Medium. Two different serum-free media were used in different aspects of the following examples: IIMD supplemented with Knockout SR (Gibco BRL) and StemPro 34 (Gibco BRL).

Methylcellulose Colony Assay. A) Blast colonies: For the generation of blast cell colonies (BL-CFC assay), EB-derived cells were plated at $0.5 \times -1.5 \times 10^5$ cells/ml in 1% methylcellulose supplemented with 10% FCS (Hyclone), vascular endothelial growth factor (VEGF; 5 ng/ml), c-kit ligand (KL; 1% conditioned medium), IL-6 (5 ng/ml) and 25% D4T endothelial cell conditioned medium (Kennedy et al. (1997) Nature 386:488-93). Transitional colonies were generated in the absence of VEGF. Colonies were scored following four days of culture. B) Hematopoietic colonies: For the growth of primitive and definitive hematopoietic colonies, cells were plated in 1% methylcellulose containing 10% plasma-derived serum (PDS; Antech), 5% protein-free hybridoma medium (PFHM-II; Gibco-BRL) plus the following cytokines: c-kit ligand (KL; 1% conditioned medium), erythropoietin (2 U/ml), IL-11 (25 ng/ml), IL-3 (1% conditioned medium), GM-CSF (3 ng/ml), G-CSF (30 ng/ml), M-CSF (5 ng/ml), IL-6 (5 ng/ml) and thrombopoietin (TPO; 5 ng/ml). Cultures were maintained at 37° C., 5% $CO_2$. Primitive erythroid colonies were scored at day 5-6 of culture, whereas definitive erythroid (BFU-E), macrophage, and multilineage colonies were counted at 7-10 days of culture. C-kit ligand was derived from media conditioned by CHO cells transfected with KL expression vector (kindly provided by Genetics Institute). IL-3 was obtained from medium conditioned by X63 AG8-653 myeloma cells transfected with a vector expressing IL-3. VEGF, GM-CSF, M-CSF, IL-6, IL-11, activin BMP2, BMP4, bFGF, FGF8, and lhh were purchased from R&D systems.

Reaggregation Cultures. Cells were cultured at $2 \times 10^5$ per ml IMDM supplemented with 15% FCS (or Knockout SR), 2 mM L-glutamine (Gibco/BRL), 0.5 mM ascorbic acid (Sigma), and $4.5 \times 10^{-4}$ M MTG in 24-well petri-grade plates. These were used to prevent adhesion of the cells to the bottom of the well.

Cardiac Muscle Assays. GFP cells were reaggregated in IMDM supplemented with 15% serum replacement. Twenty hours later the aggregates were cultured in wells of either a 24- or 96-well plate in IMDM with 10% serum replacement (serum-free). The wells were pre-treated with gelatin. Cultured were monitored daily for the development of the appearance of beating cells. Beating cells were usually detected between days 2 and 6 of culture.

Cell Surface Markers Staining and FACS Analysis. Standard conditions were used to stain the cells. Stained suspensions were analyzed on a FACScan (Becton Dickinson, Calif.).

Gene Expression Analysis. For the poly A$^+$RT-PCR analysis the method of Brady et al. ((1990) Met. in Mol. and Cell Bio. 2:17-25) was used. Reverse transcription, poly-A tailing and PCR procedures were performed as described, with the exception that the X-dT oligonucleotid was shortened to 5'-GTTAACTCGAGAATTC(T)$_{24}$-3' (SEQ ID NO:1). The amplified products from the PCR reaction were separated on agarose gels and transferred to a Zeta-probe GT membrane (Biorad) or transferred to the membrane with a slot blot apparatus (Schleicher & Schuell). The resulting blots were hybridized with $^{32}$P randomly primed cDNA fragments (Ready-to-Go Labelling, Pharmacia) corresponding to the 3' region of the genes (for all except β-H1). A β-H1-specific probe was prepared by annealing two oligonucleotides, (5'-TGGAGTCAAAGAGGGCATCATAGACACATGGG-3') (SEQ ID NO:2), 5'-CAGTACACTGGCAATCCCATGTG-3') (SEQ ID NO:3) which shares an 8 base homology at their 3' termini. This β-H1 specific oligonucleotide was labeled with $^{32}$P using a Klenow fill-in reaction. For gene specific PCR, total RNA was extracted from each sample with Rneasy mini kit and treated with RNase free DNase (Qiagen). Two microgram of total RNA was reverse-transcribed into cDNA with random hexamer using an Omniscript RT kit (Qiagen). PCR was carried out using appropriate oligonucleotides. The PCR reactions were performed with 2.5 U of Taq polymerase (Promega), PCR buffer, 2.5 mM MgCl$_2$, 0.2 uM of each primer and 0.2 mM dNTP. Cycling conditions were as follows; 94° C. for 5 min followed by 35 cycles of amplification (94° C. denaturation for 1 min, 60° C. annealing for 1 min, 72° C. elongation for 1 min) with a final incubation at 72° C. for 7 min.

EXAMPLE 2

Generation of Targeted ES Cells

Under appropriate conditions in culture, embryonic stem (ES) cells will differentiate and form three dimensional colonies known as embryoid bodies (EBs) that contain developing cell populations from a broad spectrum of lineages. Smith (2001) Annu. Rev. Cell Dev. Biol. 17:435-62. Among these EB-derived populations, one can detect mesodermal derivatives including those of the hematopoietic, endothelial, cardiac muscle and skeletal muscle lineages.

In order to track the onset of mesoderm in EBs and to isolate cells representing this population, the green fluorescence protein (GFP) was targeted to the brachyury locus. The targeting construct contained the GFP cDNA, and artificial intron, SV40 poly(A) sequences and a loxP flanked neo cassette in the first exon and is depicted in FIG. 1. The thymidine kinase (TK) gene was included at the 3 end of the targeting construct to select against random integration. The targeting vector was constructed as follows.

A BAC clone carrying the entire mouse *Brachyury* (Bry) gene was isolated by PCR screening of a 129 /Ola strain genomic library (Genome Systems) with primers 5'-AAG-GAGCTAACTAACGAGATGAT-3' (SEQ ID NO:4) and 5'-TACCTTCAGCACCGGGAACAT3' (SEQ ID NO:5). These primers anneal within the first and second Bry exon, respectively, and amplify a diagnostic band of ~600 bp. An approximately 3 kb long PstI restriction fragment carrying the 1 exon of the Bry gene along with more than 2 kb of 5' flanking region was identified and subcloned from the BAC into plasmid pBSK (Stratgene), resulting in construct pBSK.Bry-5'. Approximately 2 kb of the region immediately upstream of the start codon were sequenced to identify appropriate primer annealing sites for the construction of vectors.

Oligos 5'-GCTAGCTAATGGATC 3' (SEQ ID NO:6)/5'-GATCTGGATCCATTAGCTAGCTGCA-3' (SEQ ID NO:7) and 5-GATCTTAATGAACGGCAGGTGGGT-GCGCGTCCGGA G-3' (SEQ ID NO:8)/ 5'TCGACTCCG-GACGCGCACCCACCTGCCGTTCATTAA-3' (SEQ ID NO:9) were inserted into the PstI/SalI sites of plasmid pBSK to create a new, more suitable polylinker with two successive translational stop codons and an artificial 3' splice site (construct pBry-AA). Plasmid pEGFP.C1 (Clontech) was double-digested with NheI/BglII and the resulting ~760 bp DNA fragment encoding EGFP without stop codon was cloned into the NheI/BglII sites of pBRY-AA, resulting in construct pBry-AB. An XhoI/SalI fragment of plasmid pL2-Neo2 carrying a loxP-flanked neomycin resistance gene was inserted into the SalI site of pBry-AB to give rise to plasmid pBry-AC (transcription of EGFP and Neo in same direction).

A 556 by XmaI/MluI fragment carrying a consensus splice donor site, an artificial intron, a splice acceptor site and a short exon including the SV40 polyadenylation sequence, was excised from the commercial expression vector pBK-CMV (Stratagene). This fragment was inserted into plasmid pBry-AC in the following way: the XmaI end was ligated into the BspEI site following the last EGFP codon, whereas the Mlu end was inserted along with oligos 5'-CGCGTTACTAGTAA-GACGTCT-3' (SEQ ID NO:10)/5'-CCGGAGA CGTCT-TACTAGTAA-3' (SEQ ID NO:11) as linkers into the BspEI site located just upstream of the loxP-neo-loxP cassette. Resulting construct: pBry-AE. An ~1.9 kb XhoI/SalI fragment encoding the HSV thymidine kinase gene was inserted into the XhoI site of pBry-AE to allow selection against random integration (construct pBry-AH). A NotI/Eco47Ill fragment encoding the "short arm" of homology was excised from pBry-AF and cloned into the NotI/Eco47lII sites of pBry-AH to give rise to plasmid pBry-AI. The "long arm" of homology was excised from pBry-AK with SalI and inserted in the correct orientation into the Sail site of pBry-AI to yield final targeting vector B.

Embryonic stem cells (E14. 1, 129 /Ola Hooper et al. (1987) Nature 326:292) were electroporated with NotI-linearized targeting vector pBry-AM. Four dishes with transfected cells were subjected to G418 single-and another four dishes to G418+Gancyclovir (Ganc) double-selection. Clones that had undergone a homologous recombination event were identified by PCR with one primer (5'-CAGGTA-GAACCCACAA CTCCGAC-3')(SEQ ID NO:12) annealing to genomic sequences in the 5' region of the Bry gene, just upstream of the "short arm of homology", the other (5'-CCG-GACACGCTGAACTTGTGGC-3') (SEQ ID NO:13) to the 5' portion of EGFP (diagnostic band: approximately 1.3 kb). Correctly targeted clones were confirmed by Southern blot analysis: genomic DNA of candidate clones was digested with HincII and hybridized to a probe located outside of the targeting construct. The probe was derived from the Bry 5'flanking region (-2018 to -1249 with respect to the Bry ATG start codon) by PCR using the oiigonucleotide pair 5'-ACAG-GATCCCTAAGCCTCAAAAGAGTCGCT-3' (SEQ ID NO:14)/5'-TCTTGGATCCTCCTATCCTATC-CCGAAGCTCCT-3' (SEQ ID NO:15). 384 G418 single- and 80 G418+Ganc double-selected clones were screened, of which 4 respectively 3 proved to be positive, corresponding to a targeting efficiency of 1.04% and 3.75%. Two positive clones were transiently transfected with a modified Cre recombinase expression vector to remove the neo gene. These targeted clones are referred to hereinafter as GFP-Bry ES cells.

Brachyury is expressed transiently in developing EBs with the onset preceding the expression of genes that define the establishment of the hematopoietic and endothelial lineages. To determine whether GFP expression in GFP-Bry ES cells accurately reflects expression of the brachyury gene during EB development, GFP expression was assessed.

Figure 2A:
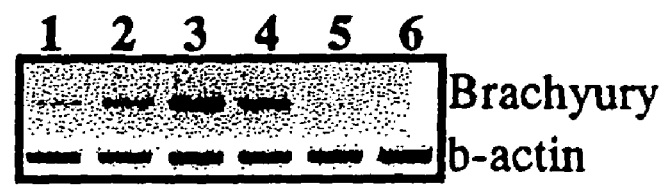
FIGS. 2A and 2B depict the expression of GFP and brachyury in developing embryoid bodies (EBs).
Figure 2B:
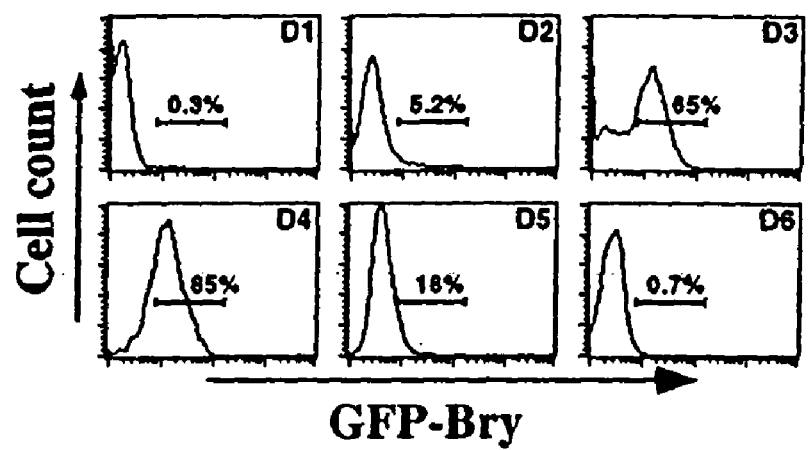

A typical expression pattern during a 6-day EB differentiation period is shown in FIG. 2A. In this experiment, low levels of message were detected within 24 hours of differentiation. Expression was upregulated over the next 48 hours, persisted through day 4 and then declined sharply to undetectable levels by day 6 of differentiation. GFP expression, as defined by FACS analysis, followed a similar temporal pattern. Low levels of GFP$^+$ cells (~5%) were detected as early as day 2 of differentiation. More than half (65%) of the EB-derived cells expressed GFP at day 3 and almost all the cells were positive at day 4 of differentiation. As observed by PCR, expression dropped sharply after this point and by day 6 few, if any, GFP$^+$ cells were present. This rapid decline in GFP expression indicated that it did not persist within the cells for extended periods of time. The high proportion of GFP$^+$ cells at days 3 and 4 of differentiation suggests that development of mesoderm within the EBs under these conditions is extensive. Taken together, these findings indicate that GFP expression accurately reflects expression of the brachyury gene during EB development.

Figure 3A:
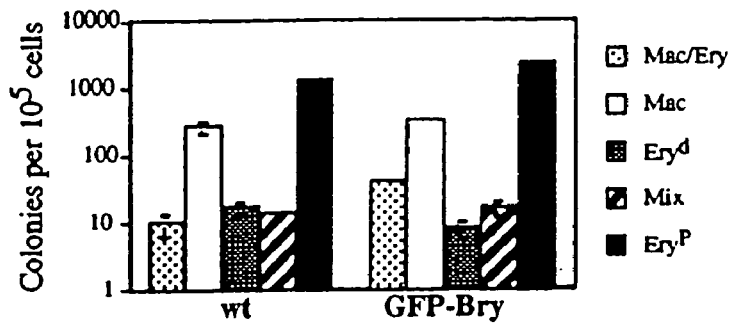
FIGS. 3A-C depict the developmental potential of wild type and GFP-Bry ES cells.
Figure 3B:
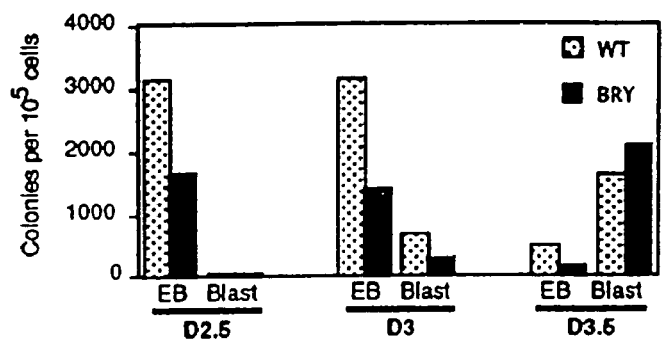
Figure 3C:
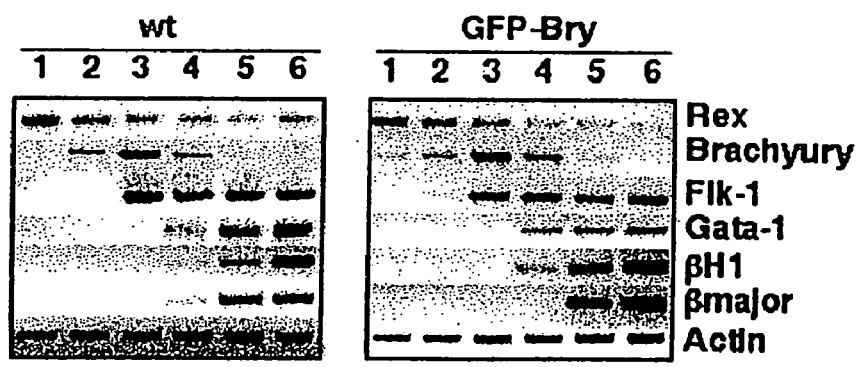

The possibility that inactivation of a single brachyury allele could have detrimental effects on the in vitro developmental potential of the ES cells was assessed. As indicated, heterozygous mice demonstrate a mild phenotype. To determine if the GFP-Bry ES cells display any detectable defects in hematopoietic development, EBs generated from them were analyzed for hematopoietic precursor and blast colony-forming cell (BL-CFC) content and for gene expression patterns. The data in FIGS. 3A and 3B indicate that GFP-Bry ES cells generate comparable numbers of primitive (Ery$^p$) and definitive (Ery$^d$, Mac, Mac/Ery, and Mix) hematopoietic precursors and BL-CFC compared to the wild type cells. Gene expression patterns (FIG. 3C) confirmed the precursor analysis and show little difference between the EBs generated from the GFP-Bry and wild type ES cells. Both sets of EBs showed a decline in Rex-1 expression over the first 3 days of differentiation. Rex-1 is a transcription factor that is expressed in ES cells and downregulated as they undergo differentiation. Rogers et al. (1991) Development 113:815-24. The decline in Rex-1 is followed by the typical transient wave of brachyury expression which immediately precedes the onset of genes involved in the development of the hematopoietic and endothelial lineages. Flk-1, a receptor tyrosine kinase essential for the establishment of these lineages (Shalaby et al. (1995) Nature 376:62-6) is expressed between day 3 and 6 of differentiation. GATA-1, a hematopoietic transcription factor, and the embryonic and adult globin genes, βH1 and βmajor, were detected at low levels at day 4 of differentiation. Expression of all 3 genes was upregulated over the next 24 hours, reflecting the expansion and maturation of the primitive erythroid lineage at this developmental stage. Palis et al. (1999) Development 126:5073-84. The precursor numbers and the gene expression patterns observed in this example are consistent with those found in previous studies and indicate that the molecular programs leading to the establishment of the hematopoietic system are intact in the targeted GFP-Bry ES cells.

EXAMPLE 3

Isolation of Brachyury$^+$ Cells

Figure 4A:
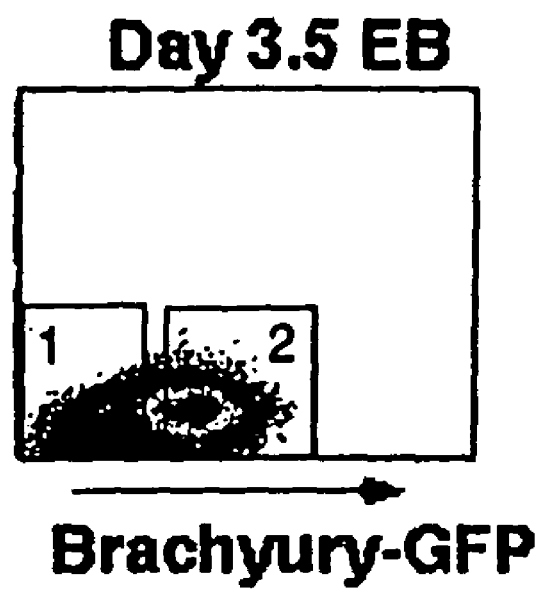
FIGS. 4A and 4B depict the gene expression profile of EB fractions isolated on the basis of GFP.

To determine if brachyury$^+$ cells could be isolated based on GFP expression, the GFP$^+$ population from day 3.5 EBs was sorted and analyzed for expression of appropriate genes. FIG. 4A shows the gates used for the isolation of the GFP positive (2) and negative (1) populations. RT-PCR analysis revealed brachyury expression was restricted to the GFP$^+$ fraction indicating that cell sorting based on GFP expression can be used to isolate brachyury$^+$ cells. Flk-1, one of the earliest makers of hematopoietic and endothelial development, was present at higher levels in GFP$^+$ that in the GFP$^-$ fraction indicating that it was expressed in at least a subpopulation of brachyury$^+$ cells. In contrast to brachyury and Flk-1, Pax-6, a gene involved in early neuronal development [79,80], was expressed at higher levels in the GFP fraction consistent with precursors of this lineage being brachyury negative. These cell-sorting studies indicate that expression of GFP under the control of the brachyury locus provides a novel marker for the isolation, characterization and manipulation of brachyury$^+$ cells from EBs.

This example demonstrates that GFP$^+$ cells can be isolated from day 3.5 EBs by cell sorting. Gene expression analysis of the GFP$^+$ and GFP$^-$ fractions shows that brachyury expression segregates predominantly to the positive fraction, a finding which clearly demonstrates that fractionation based on GFP provides a method for isolating brachyury positive cells. In addition to brachyury, the receptor tyrosine Flk-1 involved in early hematopoietic and endothelial development is also expressed at higher levels in the positive than in the negative fraction. In contrast, Rex-1 and Pax-6, markers of early ectoderm and neuroectoderm, are expressed in the GFP$^-$ fraction. These findings demonstrate that expression of GFP in the context of brachyury can be used to separate mesoderm from ectoderm.

EXAMPLE 4

Figure 4B:
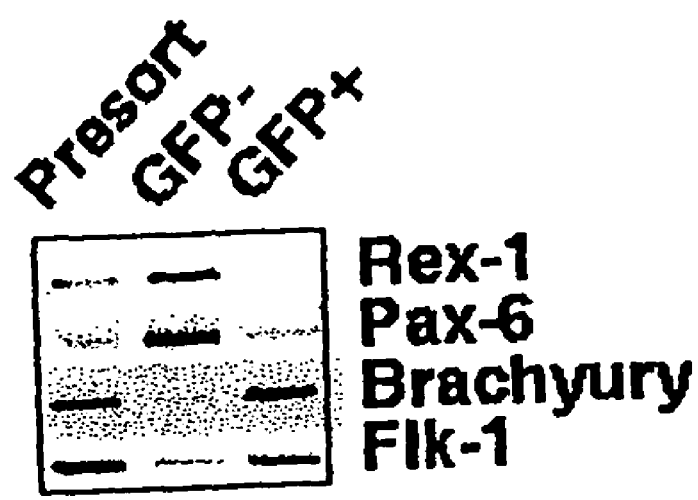

Separation of Brachyury Positive Cells into Subpopulations Based Upon Flk-1 Expression Flk-1 has been shown to be essential for the establishment of the hematopoietic and endothelial lineages in the early embryo and is expressed on the earliest precursors of these lineages, including the BL-CFC [Faloon et al. (2000) Development 127:1931-41]. Given this pivotal role in blood and vascular development, its expression within the GFP+population was hypothesized to define a subpopulation of mesoderm undergoing specification to these lineages. To investigate this possibility further, EBs were analyzed at several stages of development for the presence of GFP and Flk-1 positive cells. In the experiment illustrated in FIG. 5A, 4.8% of the day 3.0 EB population expressed GFP but not Flk-1, whereas 1.2% of the cells expressed both markers. The size of both fractions increased dramatically over the next 12 hours with the GFP$^+$/Flk-1$^-$ and GFP$^+$/Flk-1$^+$ cells representing 52% and 26% of the total EB population, respectively. To assess the developmental potential of the three populations defined by GFP and Flk-1 expression, GFP$^-$/Flk-1$^-$ (fraction 2), GFP$^+$/Flk-1$^-$ (fraction 3) and GFP$^+$/Flk-1$^+$ (fraction 4) cells were isolated at both time points and analyzed for BL- CFC and 2° EB content and for gene expression patterns. The potential of the fractions was compared to that of the pre-sorted population (fraction 1). The majority of the BL-CFC were found in the GFP$^+$/Flk-1$^+$ fraction at both day 3.0 and 3.5 of differentiation (FIG. 5B). This is not surprising given that previous studies have shown that all BL-CFC express Flk-1. The 2° EB were restricted to the GFP$^-$/Flk-1$^-$ fraction, a finding consistent with the fact that they derive from residual undifferentiated ES cells in the primary EBs. The GFP$^+$/Flk-1-fraction generated few colonies under the conditions used in these cultures. The gene expression analysis revealed some interesting differences between the populations isolated at the 2 time points (FIG. 5C). Rex-1, the ES cell marker, was expressed at lower levels in the GFP$^+$ than in the GFP$^-$ fraction, indicating that these populations are undergoing differentiation. Brachyury was expressed in the GFP$^+$ fractions at both time points. The levels appear to be higher in the GFP$^+$/Flk-1$^-$ than the GFP$^+$/Flk-1$^+$ fraction isolated from day 3.5 EBs, suggesting that its expression could be down-regulated as these cells mature towards the hematopoietic and endothelial lineages. As expected, Flk-1 was expressed predominantly in the GFP$^+$/Flk-1$^+$ cells at both time points. Scl, a helix-loop-helix transcription factor that is essential for both primitive and definitive hematopoietic development (Shivdasani et al. (1995) Nature 373:432-4), appears to be restricted to the GFP$^+$/Flk-1$^+$ fraction. Similarly, the transcription factor Runx1, required for establishment of the definitive hematopoietic system (Wang et al. (1996) Proc. Natl. Acad. Sci. 93:3444-9), was most readily detected in GFP$^+$/Flk-1$^+$ fraction. There was some Runx1 expression in the GFP$^+$/Flk-1$^-$ fraction isolated from day 3.0 EBs. Nodal is expressed in all 3 fractions at day 3 of differentiation. At day 3.5, the levels of expression in the GFP$^+$/Flk-1$^+$ fraction appear to be significantly lower than in the other fractions. Wnt3a and Wnt8a showed a remarkably restricted pattern of expression and were found only in the GFP$^+$/Flk-1$^-$ fraction at both time points, consistent with an early mesoderm function prior to the expression of lineage restricted markers. BMP2 was expressed in both GFP$^+$ fractions whereas BMP4 was found predominantly in the GFP$^+$/Flk-1$^+$ cells, indicating that these molecules play a role at distinct stages of development in this system. The BL-CFC potential and gene expression pattern of the GFP$^+$/Flk-1$^+$ cells indicates that they are representative of the extraembryonic mesoderm found in the mouse embryo.

Figure 5A:
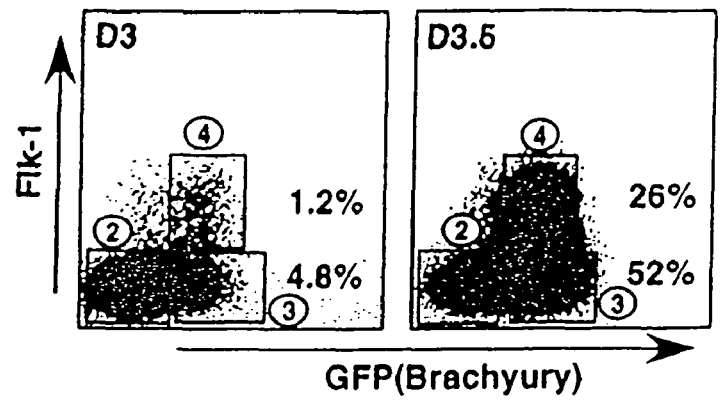
FIGS. 5A-C demonstrate the isolation and characterization of GFP and Flk-1 populations.
Figure 5B:
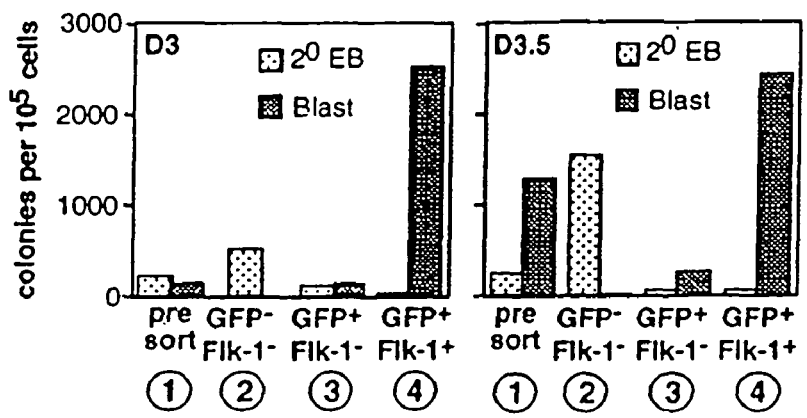
Figure 5C:
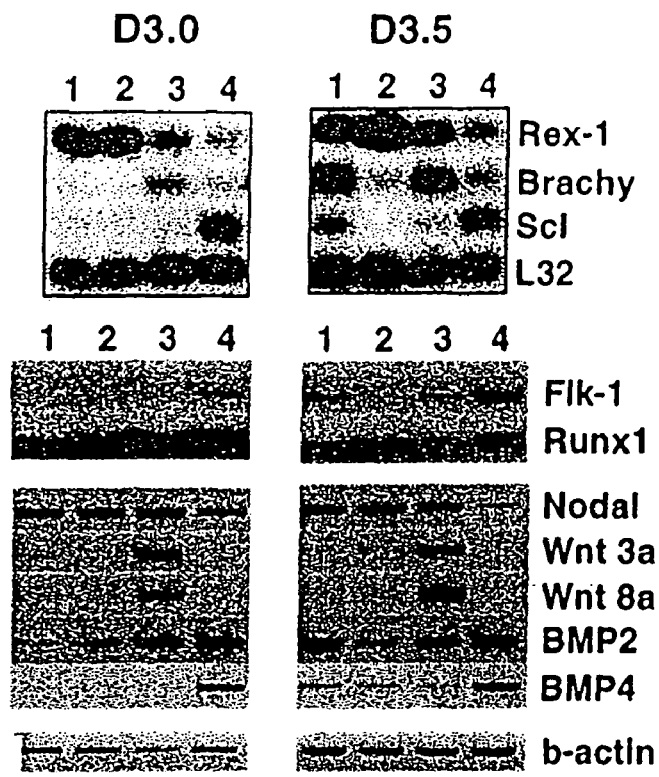

This example demonstrates that the brachyury fraction of day 3 and day 3.5 EBs can be separated into two fractions based on Flk-1 expression: brachyury$^+$/Flk-1$^-$ (GFP$^+$/Flk-1$^-$) and brachyury$^+$/Flk-1$^+$ (GFP$^+$/Flk-1$^+$) (FIG. 5A). Functional studies demonstrated that precursors (BL-CFC) able to generate both hematopoietic and endothelial cell segregated to the (GFP$^+$/Flk-1$^+$) fraction, suggesting that upregulation of Flk-1 is indicative of commitment to these lineages (FIG. 5B). Gene expression studies demonstrated distinct differences between the GFP$^+$/Flk-1$^-$ and GFP$^+$/Flk-1$^+$ populations (FIG. 5C).

EXAMPLE 5

Developmental Relationships Among the GFP/FLK Fractions

Figure 6:
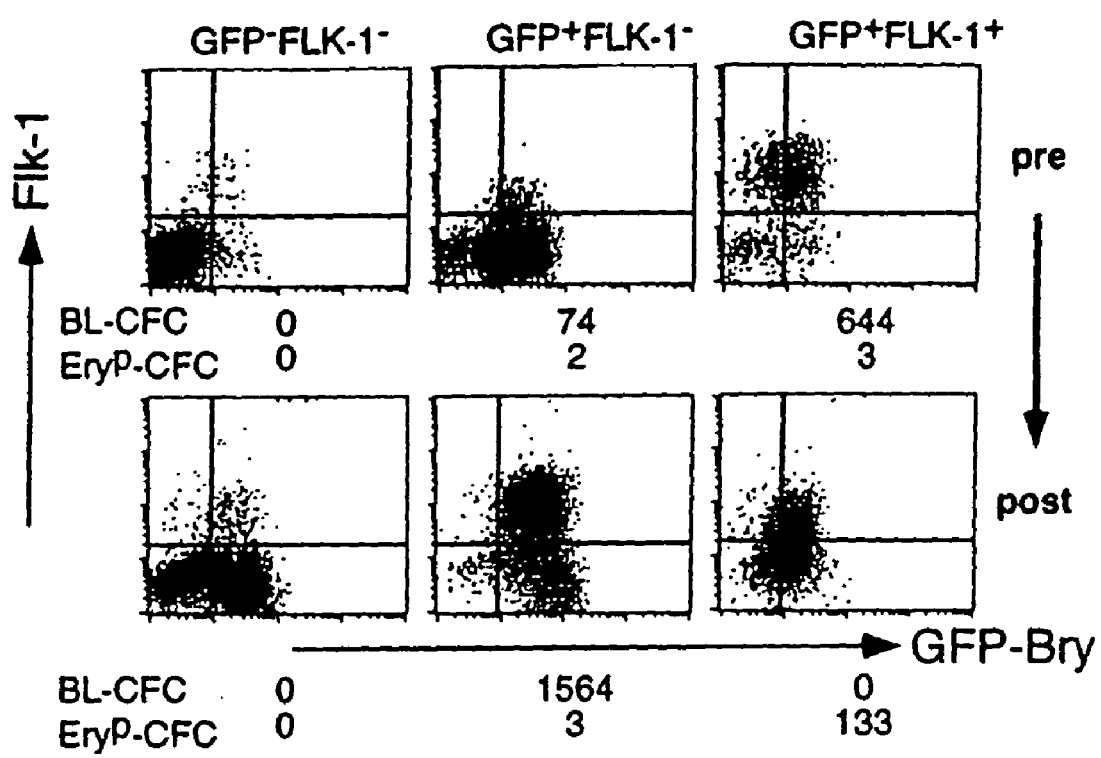
FIG. 6 depicts the expression of GFP and Flk-1 in isolated day 3 EB-derived fractions. The top row shows the expression profiles of the three fractions prior to culture (pre). The bottom row indicates the profile of the same cell populations following 20 hours of culture (post). The numbers below each profile indicate the BL-CFC and primitive erythroid (Ery$^P$-CFC) potential (precursors per 1×10$^5$ cells plated) of each population.

The expression patterns observed in FIG. 5 are consistent with the interpretation that the three fractions represent a developmental continuum with the GFP$^-$/Flk-1$^-$ cells giving rise to the GFP$^+$/Flk-1$^-$ cells which in turn give rise to the GFP$^+$/Flk-1$^+$ cells. To determine if these fractions do represent specific stages within a common developmental pathway, each was isolated from day 3 EBs, cultured for 20 hours and then re-analyzed for GFP and Flk-1 expression. BL-CFC and Ery$^p$-CFC potential was determined for each of the populations prior to and following culture. The isolated cells were cultured at densities of 1×10$^5$ cells or greater in petri-grade 24-well plates in the same medium used for EB differentiation. Under these conditions, the cells rapidly reaggregate and form EB-like structures that appear to follow a normal developmental program with little expansion or loss in cell number. Following the 20-hour reaggregation culture, the GFP$^-$/Flk-1$^-$ cells gave rise to a significant population of GFP$^+$/Flk-1$^-$ cells as well as to a small number of GFP$^+$/Flk-1$^+$. GFP$^+$/Flk-1$^-$ cells generated a substantial population of GFP$^+$/Flk-1$^+$ cells during the same culture period. The GFP$^+$/Flk-1$^+$ population appeared to lose some GFP and Flk-1 expression following the reaggregation culture. Results are shown in FIG. 6. The changes in precursor potential were consistent with the changes in surface markers. The GFP$^-$/Flk-1$^-$ fraction, the most immature of the three, contained an undetectable number of BL-CFC and Ery$^p$-CFC before or after culture. The GFP$^+$/Flk-1-fraction also contained few BL-CFC and Ery$^p$-CFC prior to culture. However, following culture, the BL-CFC potential increased dramatically, from 74 to 1564 per 10$^5$ cells, consistent with the increase in Flk-1 expression. The frequency of Ery$^p$-CFC did not change during the culture period. The GFP$^+$/Flk-1$^+$ fraction contained BL-CFC but few Ery$^p$-CFC prior to culture. No BL-CFC were detected following culture, however, the population now contained Ery$^p$-CFC. Together with the surface marker analysis, these precursor data support a developmental progression from a pre-mesoderm (GFP$^-$/Flk-1$^-$) to a mesoderm/pre-hemangioblast (BL-CFC) population (GFP$^+$/Flk-1$^-$) to a hemangioblast/pre-erythroid population (GFP$^+$/Flk-1$^+$) to a post hemangioblast/erythroid population (possibly GFP$^{lo}$/Flk-1$^{lo}$). Not all the cells in a given population appear to differentiate following the 20-hour culture period as cells with the starting phenotype persisted in the GFP$^-$/Flk-1$^-$ and GFP$^+$/Flk-1$^-$ cultures.

This example indicates that when isolated and recultured for 20-24 hours, each of the three populations isolated from day 3 EBs continued to differentiate and in a pattern that indicates that these populations represent a developmental continuum. For instance, GFP$^-$/Flk-1$^-$ gave rise to GFP$^+$/Flk-1$^-$ cells which in turn gave rise to GFP$^+$/Flk-1$^+$. These changes in cell surface characteristics were associated with the expected changes in developmental potential. The GFP$^+$/Flk-1$^-$ fraction contained few hematopoietic/endothelial precursors (BL-CFC) prior to culture. Following culture, these precursors were detected, clearly demonstrating that the GFP$^+$/Flk-1$^-$ fraction from day 3 EBs does contain the potential to give rise to Flk-1$^+$ cells with hematopoietic and endothelial potential.

EXAMPLE 6

Potential of GFP/Flk-1$^-$ Cells

Figure 7A:
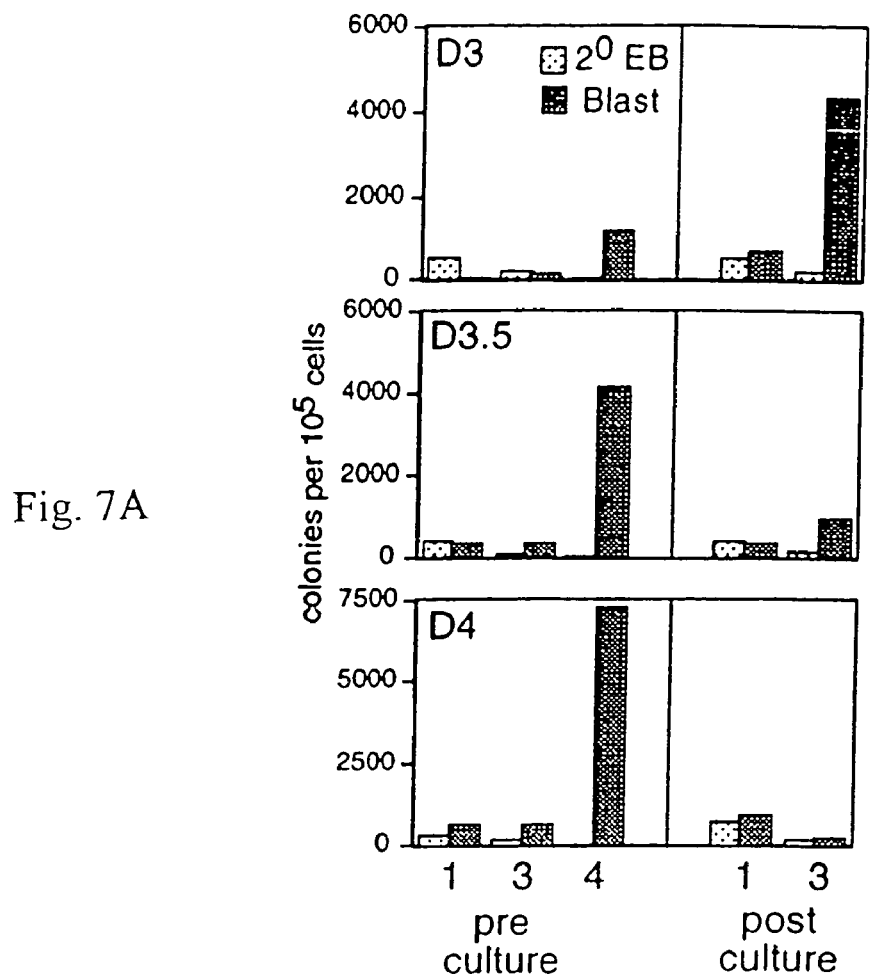
FIGS. 7A and 7B depict the BL-CFC potential and Flk-1 expression of the isolated cell populations prior to and following culture.
Figure 7B:
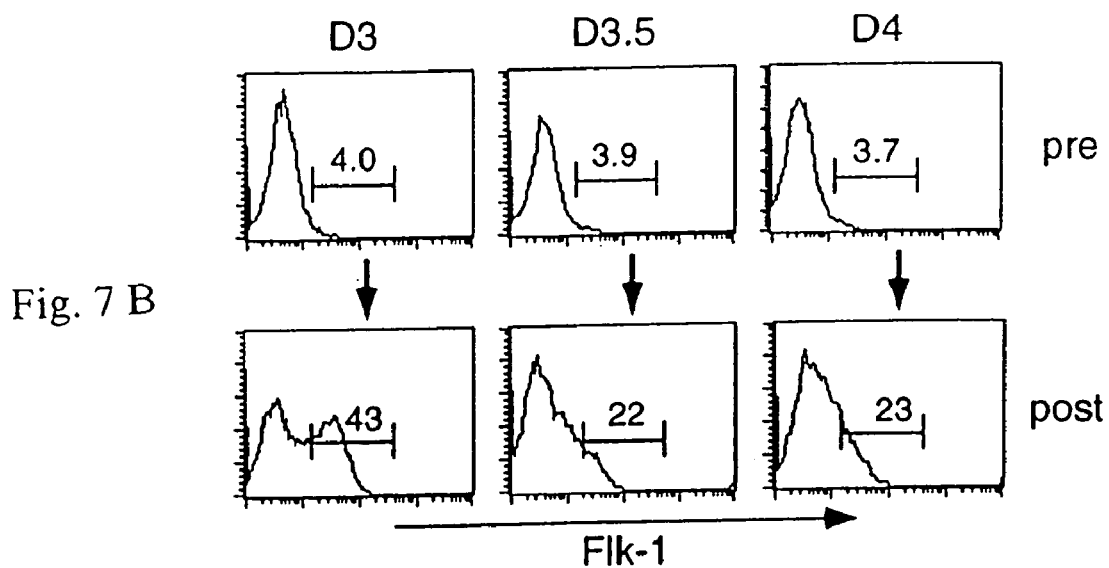

The foregoing examples demonstrated that GFP$^+$/Flk-1$^-$ cells isolated from day 3.0 EBs efficiently generated GFP$^+$/Flk-1$^+$ cells and BL-CFC following overnight culture. To determine if this pre-BL-CFC potential was specific to the GFP$^+$/Flk-1$^-$ fraction isolated at this stage of development, GFP$^+$/Flk-1$^-$ cells from different aged EBs were assayed for their ability to give rise to BL-CFC. As shown in FIG. 7A, the capacity to generate BL-CFC was most robust in the day 3 GFP$^+$/Flk-1$^-$ cells. This developmental potential decreased dramatically by day 3.5 of differentiation and was almost non-existent at day 4.0. The BL-CFC content of the freshly isolated GFP$^+$/Flk-1$^+$ fraction from these same EBs increased over this period of time, indicating that differentiation was progressing in a normal fashion. The Flk-1 expression patterns in the reaggregated cultures from the different staged EB cells were consistent with BL-CFC data. The cultures from the reaggregated day 3.0 GFP$^+$/Flk-1$^-$ cells contained a distinct Flk-1 fraction that represented more than 40% of the total population (FIG. 7B). Flk-1 expression in the day 3.5 and 4.0 cultures was significantly lower and consisted of a shoulder of the total population rather than a distinct peak.

EXAMPLE 7

Cardiomyocyte Potential of GFP and Flk-1 Subpopulations

Given the sequence of events in the mouse embryo in which the development of hematopoietic and endothelial mesoderm is followed by the development of cardiac and cranial mesoderm, the cardiomyocyte potential of the isolated populations was determined. For this analysis, aggregates from the cultures of the different populations were transferred to microtiter or 24-well plates in serum-free medium and monitored for the development of beating cell masses, indicative of cardiomyocytes. These conditions are known to support the efficient development of cardiomyocytes from the reaggregated cells. As an independent confirmation of the cardiomyocyte nature of the cells within these masses, a representative group was transferred to microscope slides, fixed and stained for the presence of the cardiac-specific isoform of Troponin T. All beating cell masses analyzed were found to contain Troponin T positive cells indicating that they were cardiomyocytes. Using this assay, the cardiomyocyte potential of the reaggregated GFP$^+$/Flk-1$^-$ and GFP$^+$/Flk-1$^+$ fractions from different staged EBs was determined. For comparison, the BL-CFC potential of the freshly isolated GFP$^+$/Flk-1$^+$ cells and of the cultured GFP$^+$/Flk-1$^-$ cells was analyzed.

TABLE I

BL-CFC, pre-BL-CFC and cardiomyocyte potential of the GFP+/Flk-1− and GFP+/Flk-1+ fractions isolated from different staged EBs.

| EB Age | GFP$^+$ Flk$^-$ | | GFP$^+$ Flk$^+$ | |
|---|---|---|---|---|
| | BL-CFC following culture | beating following culture | BL-CFC direct plating | beating following culture |
| 2.75 | +++ | − | + | − |
| 3.5 | + | ++ | +++ | − |
| 4.0 | +/− | ++ | +++ | − |

As shown in Table 1, the BL-CFC potential of the different fractions was similar to that observed in previous experiments. The GFP$^+$/Flk-1$^+$ cells isolated from the three different EB populations generated BL-CFC, with the highest number found at day 3.5 and 4.0. The pre-BL-CFC potential in the GFP$^+$/Flk-1$^-$ cells was greatest at day 2.75 and decreased significantly at 3.5 and 4.0. The cardiomyocyte potential of the fractions showed a reverse pattern. A significant proportion (>80%) of the transferred aggregates from day 3.5 and 4.0 GFP$^+$/Flk-1$^-$ cells generated beating cardiomyocytes. No beating cells were observed in the aggregates generated from the earliest (day 2.75) GFP$^+$/Flk-1$^-$ cells. Beating cells were not detected in aggregates generated from the GFP$^+$/Flk-1$^+$ cells isolated from EBs at any of the three stages of development. The findings from this analysis are consistent with the notion that GFP$^+$/Flk-1$^-$ cells isolated at different stages have different potentials. Those that develop early appear to have a hemangioblast fate, whereas those that develop later generate the cardiac lineage and possibly other populations. The GFP$^+$/Flk-1$^+$ populations appear to have lost the cardiomyocyte potential and may be restricted to the hemangioblast lineages. Given these findings, the early developing (day 2.75-3.0) GFP$^+$/Flk-1$^-$ cells are referred to as pre-hemangioblast mesoderm whereas the population that develops between day 3.5 and 4.0 are referred to as pre-cardiac mesoderm. The day 3.0-3.5 GFP$^+$/Flk-1$^+$ populations generate BL-CFC, whereas those isolated from later stage EBs (day 4.0) contain primitive erythroid progenitors, indicating the onset of hematopoietic commitment. Given this developmental potential, the GFP$^+$/Flk-1$^+$ population is referred to as hemangioblast mesoderm.

Examples 5 and 6 demonstrate that GFP+ cells isolated from different aged EBs have different developmental potential. As indicated in the previous examples, GFP$^+$/Flk-1$^-$ cells from day 3 EBs efficiently generate both hematopoietic and endothelial lineages. These cells did not give rise to cardiotiyocytes (heart tissue) as demonstrated by the lack of beating cell masses. In contrast, GFP$^+$ cells from day 4 EBs gave rise to few Flk-1$^+$ cells and BL-CFC following culture. This population did, however, generate cells of the cardiomyocte lineage. These findings demonstrate that the GFP$^+$ (brachyury$^+$) fraction isolated from different aged EBs have become patterned to distinct populations with different developmental fates. In addition to the conditions used and potentials observed in the foregoing examples, other potentials may be observed by altering conditions and additives.

EXAMPLE 8

Role of Serum-Derived Factors

To assess the role of serum in the development of brachyury$^+$ cells, EBs were differentiated the absence of serum. EBs did develop under these conditions, although they were somewhat smaller than those found in normal conditions. In the absence of serum, no GFP$^+$ cells were detected within these EBs, indicating that mesoderm was not induced under these conditions (FIG. 8). Significant numbers of GFP$^+$/Flk$^-$ and GFP$^+$/Flk-1$^+$ cells did develop when serum was added to the cultures. These findings clearly demonstrate that components found within serum are able to induce the development and differentiation of brachyury$^+$ cells. As a first step in identifying factors that might play a role in this process, BMP4 (20 ng/ml) was added to the developing EBs in the serum free cultures. At this concentration, BMP4 did induce a significant population of brachyury$^+$ cells within 3 days of differentiation. However, in contrast to the serum, BMP4 did not support the development of the GFP$^+$/Flk-1$^+$ population in this period of time. To determine if BMP4 could induce GFP$^+$/Flk-1$^+$ from GFP$^+$/Flk-1$^-$ cells that were induced in the presence of serum, GFP$^+$/Flk-1$^-$ cells were isolated from EBs differentiated for three days in the presence of serum. These cells were reaggregated in medium alone, in medium with serum or in medium with BMP4. As shown in the lower row of FIG. 8, GFP$^+$/Flk-1$^-$ cells did not differentiate substantially when reaggregated in the absence of serum. As expected, the same population generated a large GFP$^+$/Flk-1+population when serum was added to the cultures. Consistent with the findings in the primary differentiation cultures, BMP4 was unable to induce the development of significant numbers of GFP⁺/Flk-1⁺ cells from the cultured GFP⁺/Flk-1⁻ cells.

Figure 9:
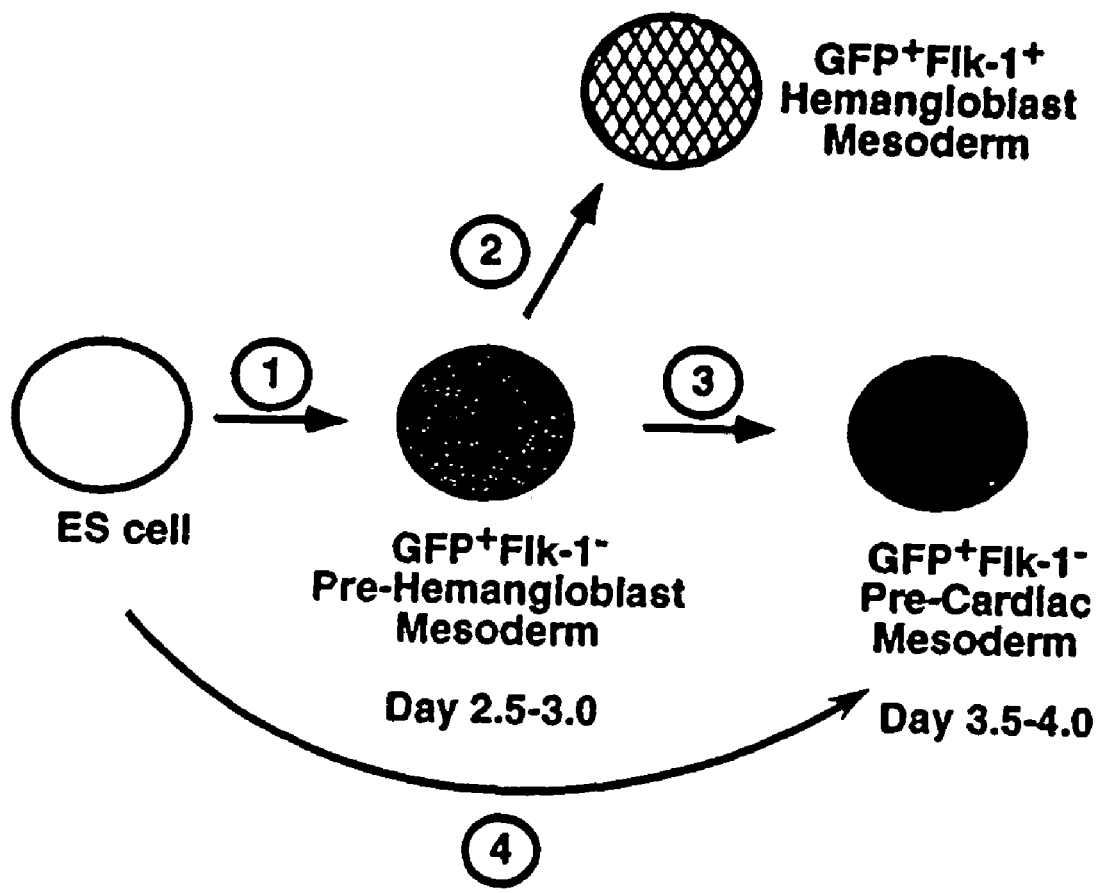
FIG. 9 is a schematic model of mesoderm formation and specification in EBs.

FIG. 9 summarizes the stages in mesoderm development based upon the foregoing examples. Step #1 represents mesoderm induction and patterning to a pre-hematopoietic and endothelial (pre-hemangioblast) fate. Step #2 represents specification to the hematopoietic and endothelial lineages. Steps #3 and #4 represent patterning to the pre-cardiac fate.

EXAMPLE 9

Isolation and Characterization of Endoderm Potential of Cell Populations

Figure 10:
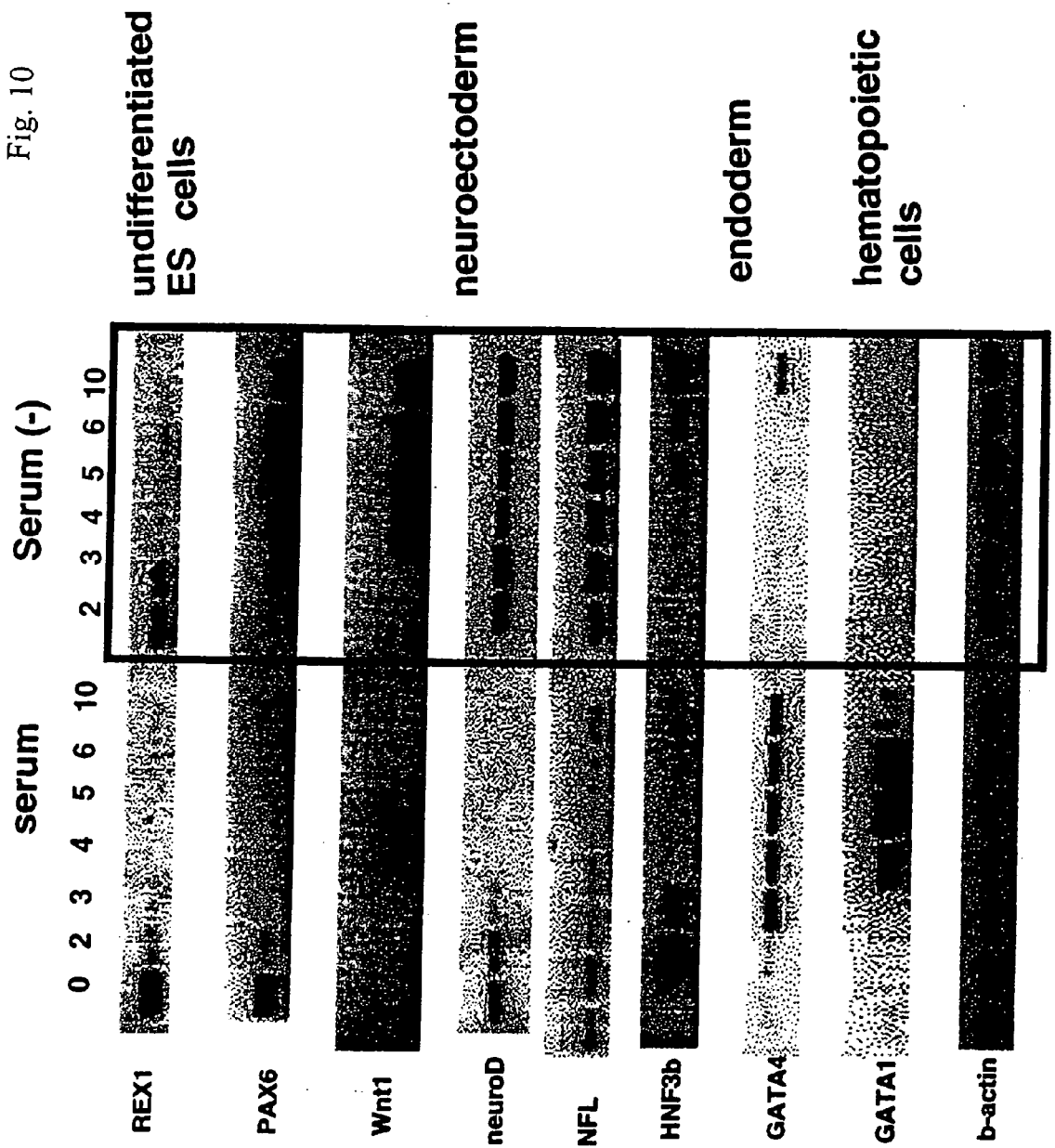
FIG. 10 shows the expression of genes in EBs in the presence and absence of serum.
Figure 11:
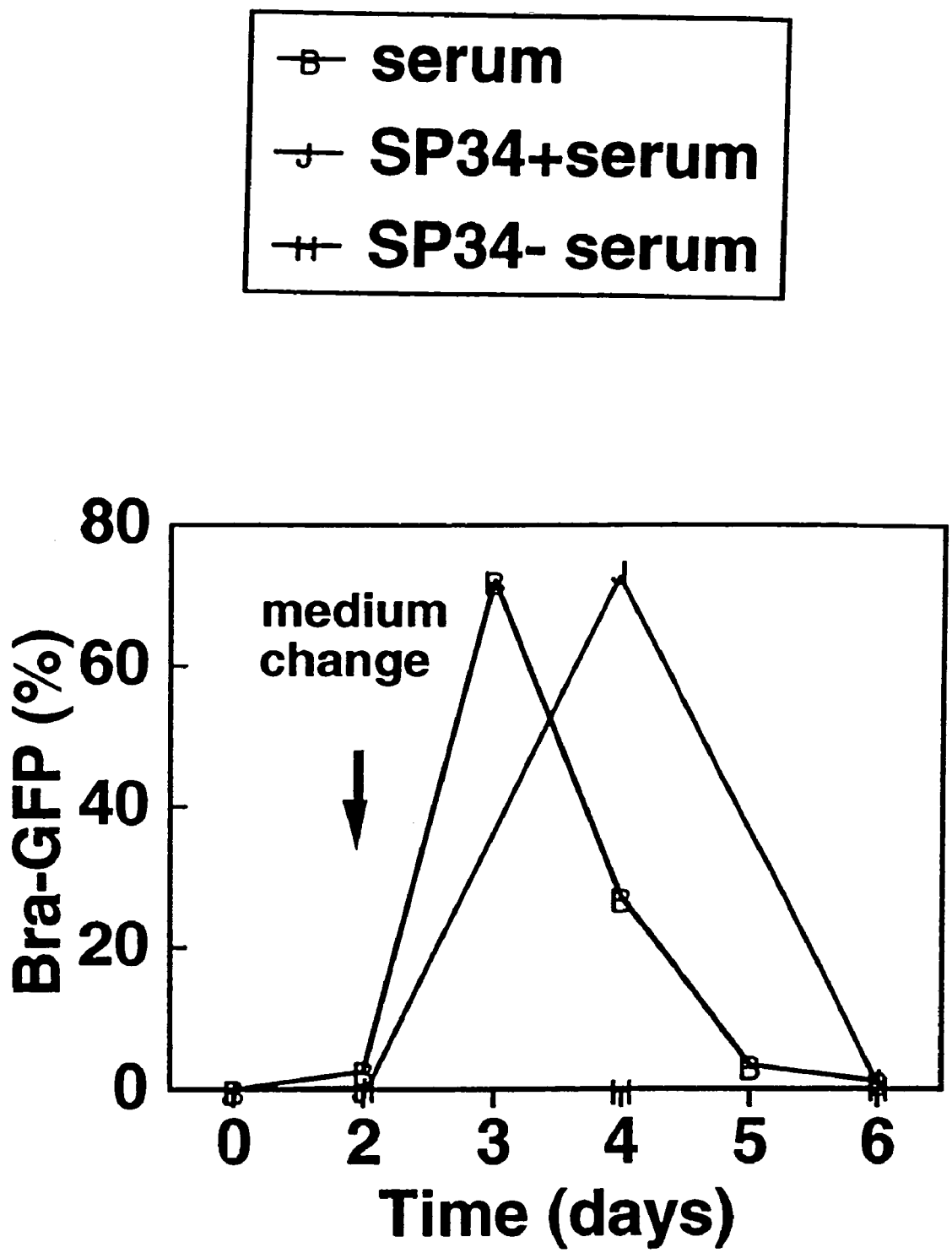
FIG. 11 is a graph depicting brachyury expression in EBs generated under different conditions.
Figure 12:
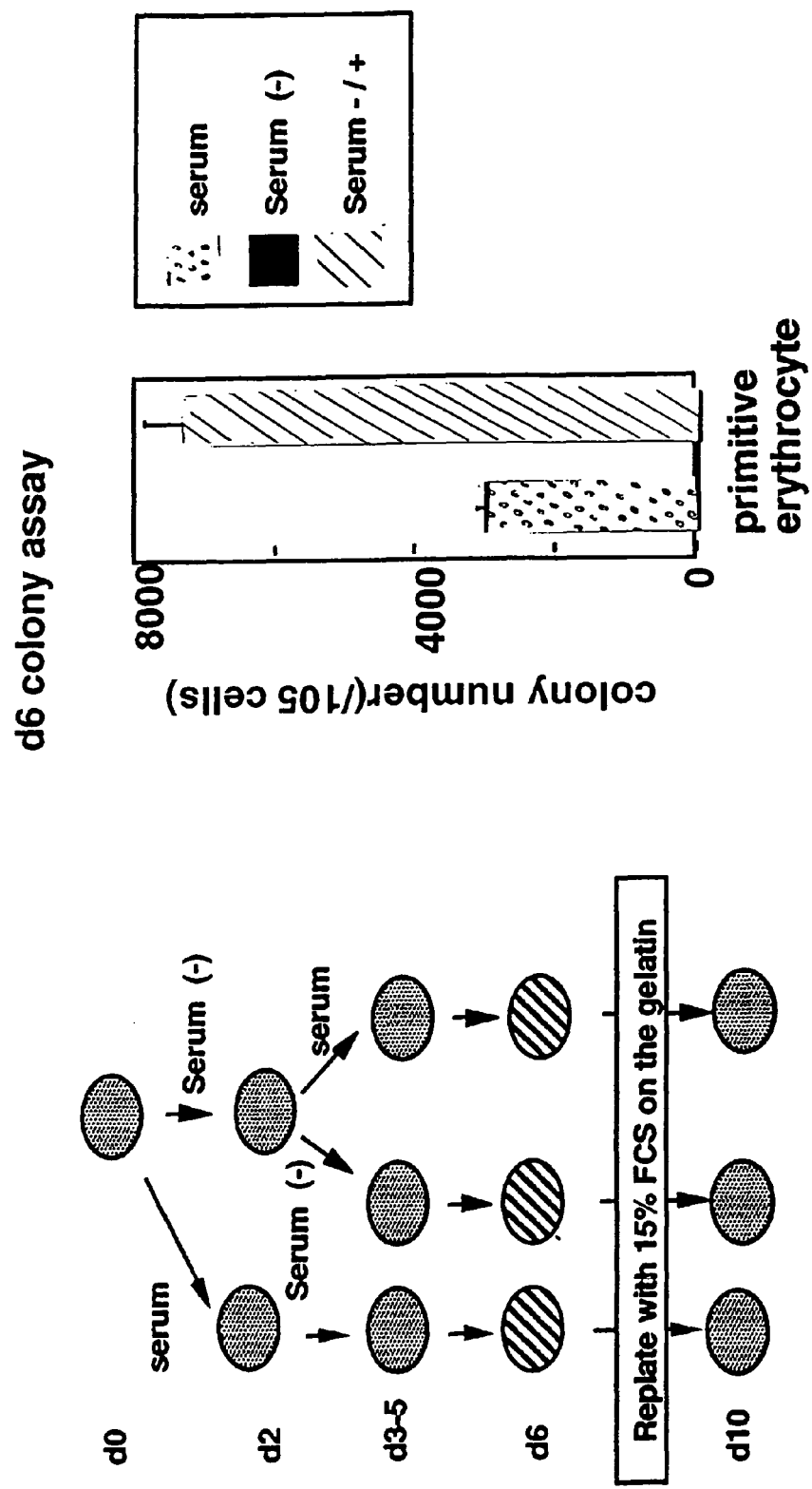
FIG. 12 shows that EBs grown in serum contained hematopoietic precursors, whereas those grown without serum did not.
Figure 13:
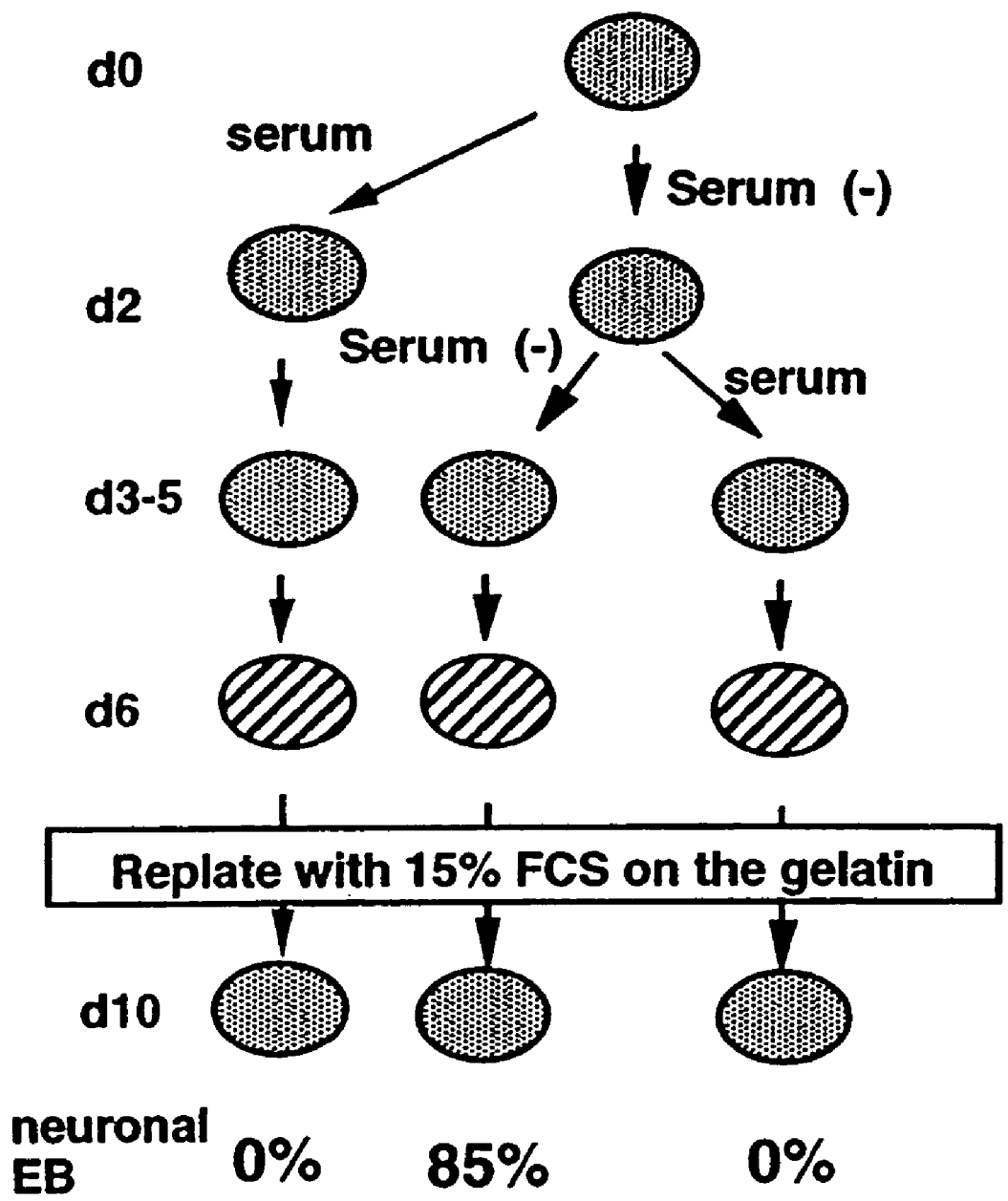
FIG. 13 is a schematic diagram showing neuronal differentiation is the presence and absence of serum.

Studies using model systems such as Xenopus and Zebrafish have suggested that mesoderm and endoderm develop from a common precursor population known as mesendoderm. To determine whether or not a mesendoderm stage of development does exist in EBs, conditions for the development of the endoderm lineage were established. As a first step in establishing culture conditions for the development of this lineage, the amount of serum in the differentiation cultures was varied. EBs were generated in the presence and absence of serum (SP34 and then IMDM plus SR) and assayed at different stages for expression of genes associated with ectoderm, endoderm and mesoderm development. For the ectoderm lineage, development of the neuronal lineage was assessed analyzing expression of PAX6, Wntl, neruoD and neurofilament (NFL). These genes are known to be expressed at different stages of neruonal development. The early stages of endoderm development were monitored by expression of HNF3β. To evaluate later stages of endoderm development and specification, genes involved in liver development were analyzed. These included Hex, α-fetoprotein (AFP), HNF4, Albumin (Alb), α-1-antittrypsin (AAT) and tyrosine aminotransferase (TAT). Mesoderm development was monitored by expression of brachyury and GATA-1. In addition to gene expression patterns, neuronal development was assayed by monitoring neurite outgrowth from EBs. The neuronal nature of these neurites was demonstrated by βIII-Tubulin expression. Mesoderm development was also assessed by enumeration of hematopoietic progenitors in the EBs. FIG. 10 shows the impact of serum on the developmental potential of EBs over a 10-day differentiation period. In the presence of serum (serum) there is little neuro-ecotderm differentiation as demonstrated by the lack of expression of the genes associated with development of this lineage. HNF3β is expressed at early stages of differentiation (day 2-3) and then downregulated. As expected, GATA-1 is expressed in the EBs generated under these conditions. The pattern of expression of these genes was basically reversed in EBs grown in the absence of serum (serum−). These EBs expressed all the genes associated with neuroectoderm, but did not express the mesoderm/hematopoietic marker GATA-1. HNF3β was expressed in late stage EBs (day 10) grown under these conditions. The patterns of brachyury expression as monitored by GFP expression were consistent with these findings. EBs generated in the presence of serum generated a substantial brachyury⁺ population that was present between days 2 and 5 of differentiation (FIG. 11, -B-line). Brachyury was not detected in EBs grown in the absence of serum (FIG. 11, -H-line). Hematopoietic precursor assays confirmed these findings. EBs generated in serum contained precursors (FIG. 12, speckled bar), whereas those grown without serum did not (FIG. 12, solid bar, not visible). Finally, evaluation of neurite potential of the EBs was consistent with these various analyses. None of the EBs grown in serum generated neurites. In contrast, 85% of those generated in the absence of serum displayed this activity (FIG. 13). Taken together, these findings demonstrate the importance of culture conditions (serum) for the generation of specific lineages. They also demonstrate that neither serum complete nor serum-free-conditions were optimal for endoderm development.

Figure 14:
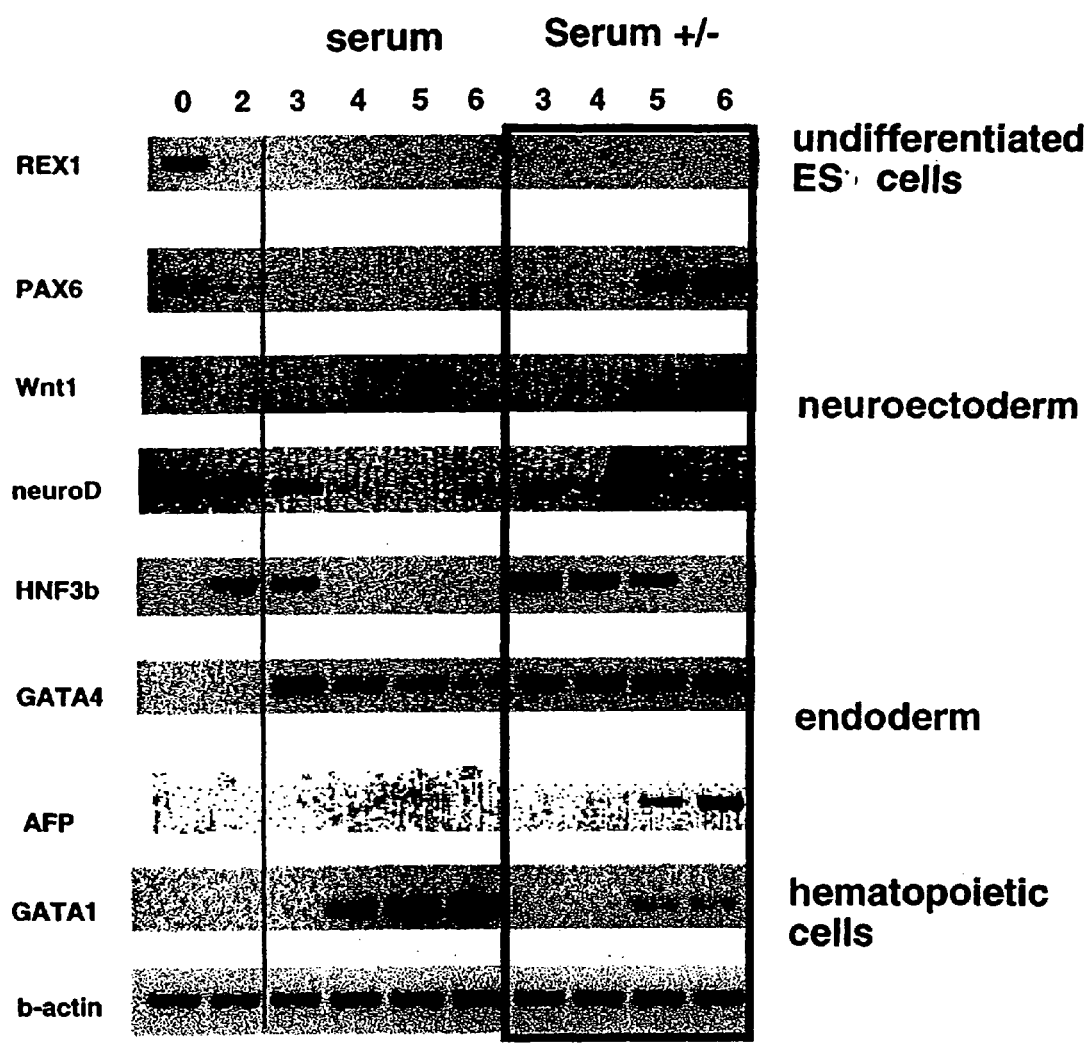
FIG. 14 shows the expression of genes in EBs initiated for two days in serum and then switched to serum free conditions.
Figure 15:
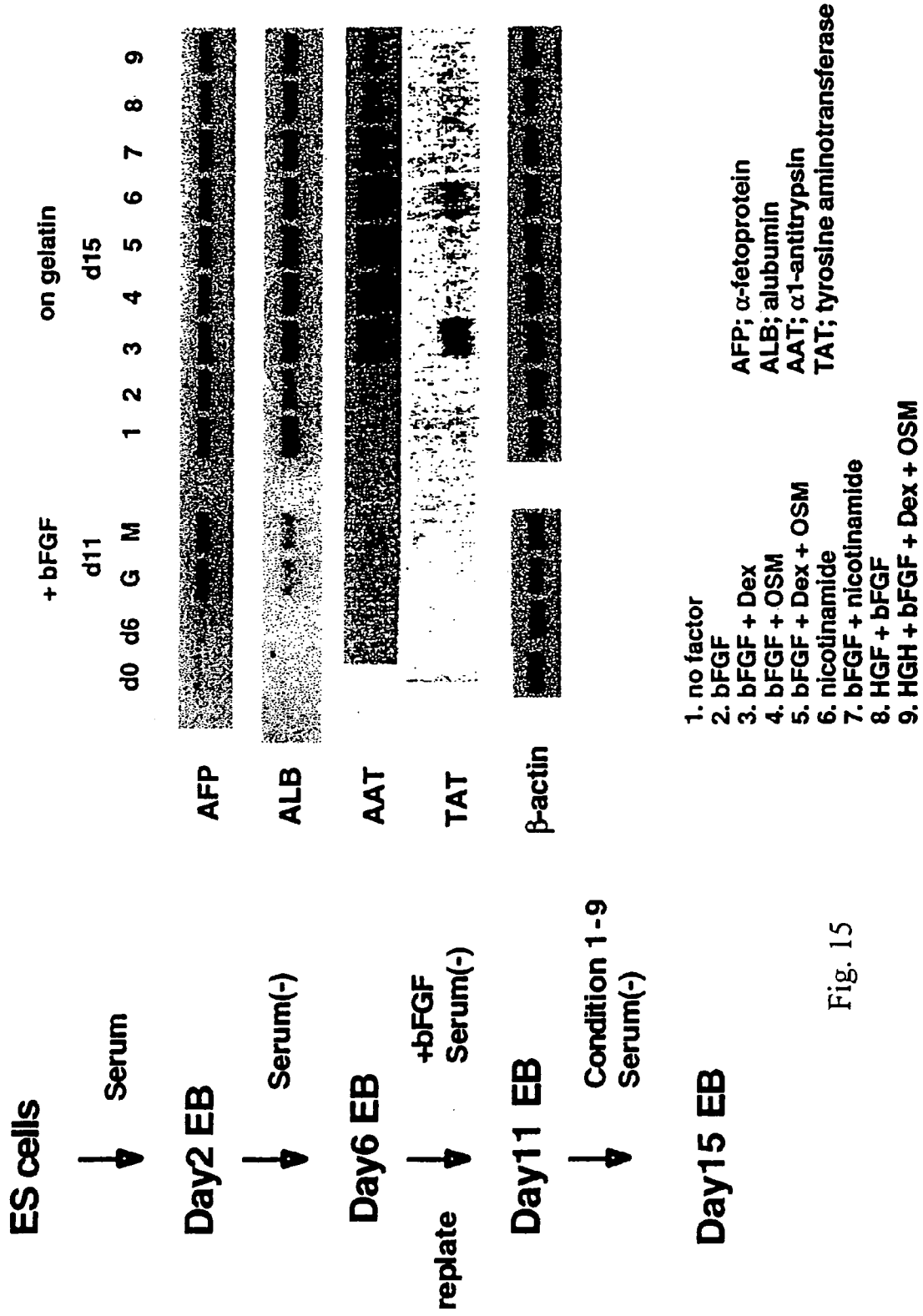
FIG. 15 shows gene expression in EBs cultured in the presence of bFGF.

The strong upregulation of HNF3β in the early stage EBs generated in serum suggested that serum might be important for the establishment, but not the maturation of the endoderm lineage. To test this possibility, EBs were initiated for 2 days in the presence of serum and then switched to serum-free conditions (SR). As shown in FIG. 14, EBs generated under these conditions (serum+/−) expressed HNF3β between days 3 and 5 of differentiation. AFP was upregulated at day 5 of differentiation. GATA-1 expression levels were reduced compared to those found in serum-stimulated EBs. Next, day 6 EBs generated under the serum+/− conditions were plated in tissue culture grade dishes (to allow them to adhere) in the presence of the growth factor bFGF. The dishes were coated with either gelatin or matrigel to determine if substrate had any impact on further endoderm differentiation. Five days later, the medium was changed and additional factors were added to these cultures to promote the development of the liver lineage. The experimental outline and data are shown in FIG. 15. In this experiment AFP was not expressed at the day 6 EB stage. Its levels of expression were upregulated when cultured in the presence of bFGF on either gelatin of matrigel. Low levels of ALB were also detected at this stage. ALB expression increased following the additional culture period in all conditions tested. AAT and TAT were also expressed following the last culture step. The highest levels of TAT were found when EB-derived cells were cultured in the presence of bFGF and Dex. These findings clearly indicate that it is possible to generate cells of the endoderm lineage and that under appropriate conditions, they will give rise to cells that express genes associated with the developing liver.

Figure 16:
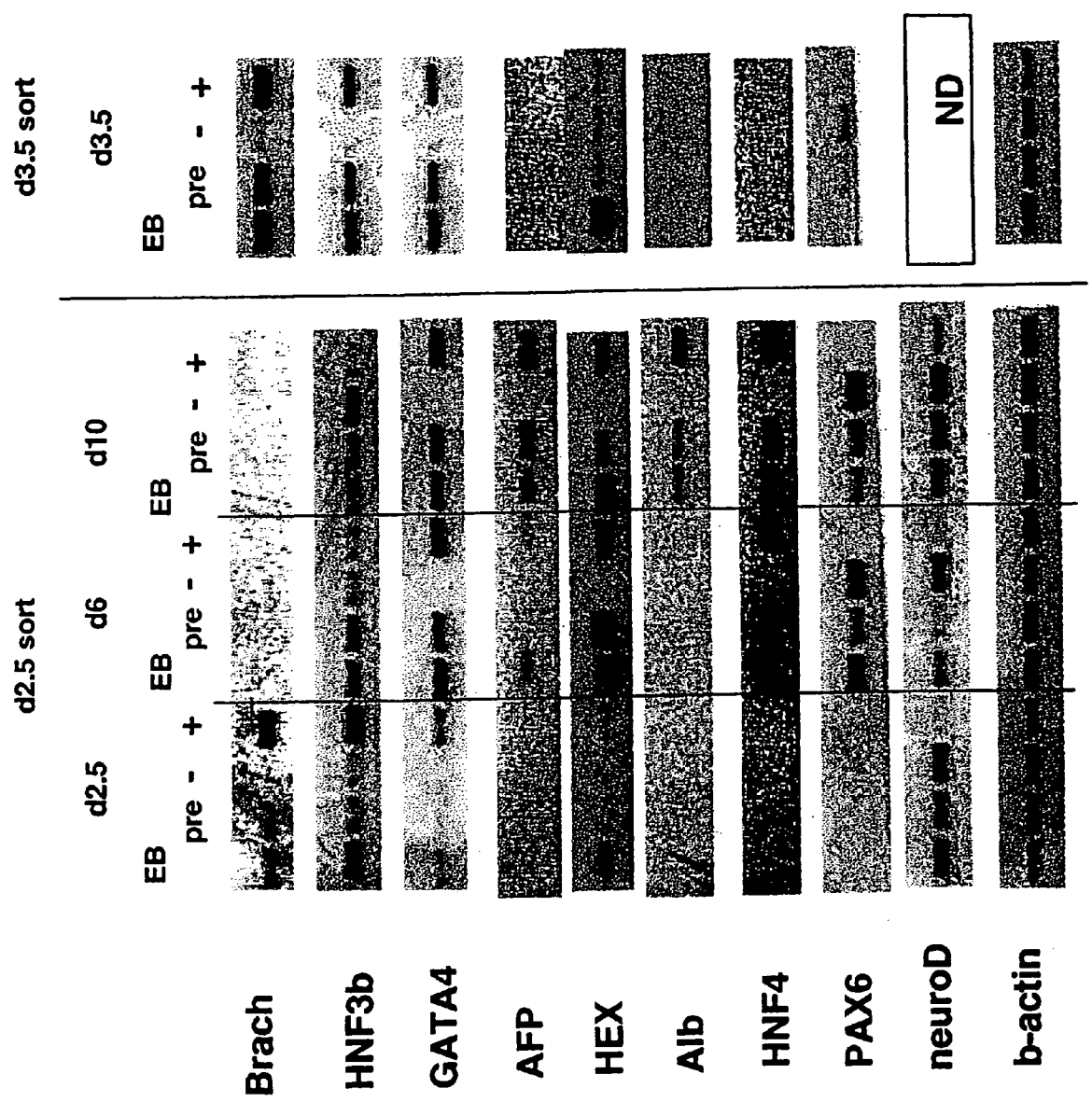
FIG. 16 shows gene expression patterns in Bry$^+$ and Bry$^-$ cells cultured in the presence of bFGF.

It was further determined if these endodermal cells developed from brachyury⁺ or brachyury⁻ cells. To address this question, GFP (Bry)⁺ and GFP (Bry)⁻ cells were isolated from day 2.5 EBs by cell sorting. These populations were allowed to reaggregate and cultured as clusters until day 6. On day 6, they were moved to the tissue culture grade dishes in medium with bFGF for 4 days (total of 10 days). Gene expression analysis indicated that cells, which express HNF3β, segregated to the GFP⁺ fraction (d2.5) (FIG. 16). With time in culture, this gene was expressed in cells generated from the GFP fraction. This likely reflects the fact that at later stages of expression HNF3α is expressed in non-endodermal population. AFP, HEX, ALB and HNF4 were all expressed in derivatives of the GFP⁺ fraction, but not in cell populations generated from the GFP-cells. In contrast, PAX6 and neuroD, markers of neuroectoderm, were found predominantly in cells generated from the GFP⁻ fraction. These findings indicate that the endoderm lineage is established from a brachyury⁺ population, which also gives rise to the mesodermal lineage, and that these lineages derive from a common precursor, the mesendoderm.

To further evaluate the liver potential of the brachyury expressing cells, cell populations derived from both the bry⁺ and bry⁻ fractions were analyzed for expression of genes representing early hepatocyte development such as α-fetoprotein (AFP), albumin (ALB) and transthyretin (TTR) and genes indicative of maturation of the lineage including alpha1-antitrypsin (AAT), tyrosine aminoferase (TAT) and carbamoyl phosphate synthetase I (CPase). β-actin expression was used as a control. Cells were analyzed prior to sorting and subsequent to sorting into bry⁺ and bry⁻ populations. Fetal liver and adult liver controls were also analyzed. Expression of all of these genes was restricted to the cells derived from the bry⁺ population, indicating that cells with hepatocyte characteristics develop from brachyury expressing cells.

EXAMPLE 10

Kinetics of Mesoderm and Endoderm Development in EBs

Figure 18:
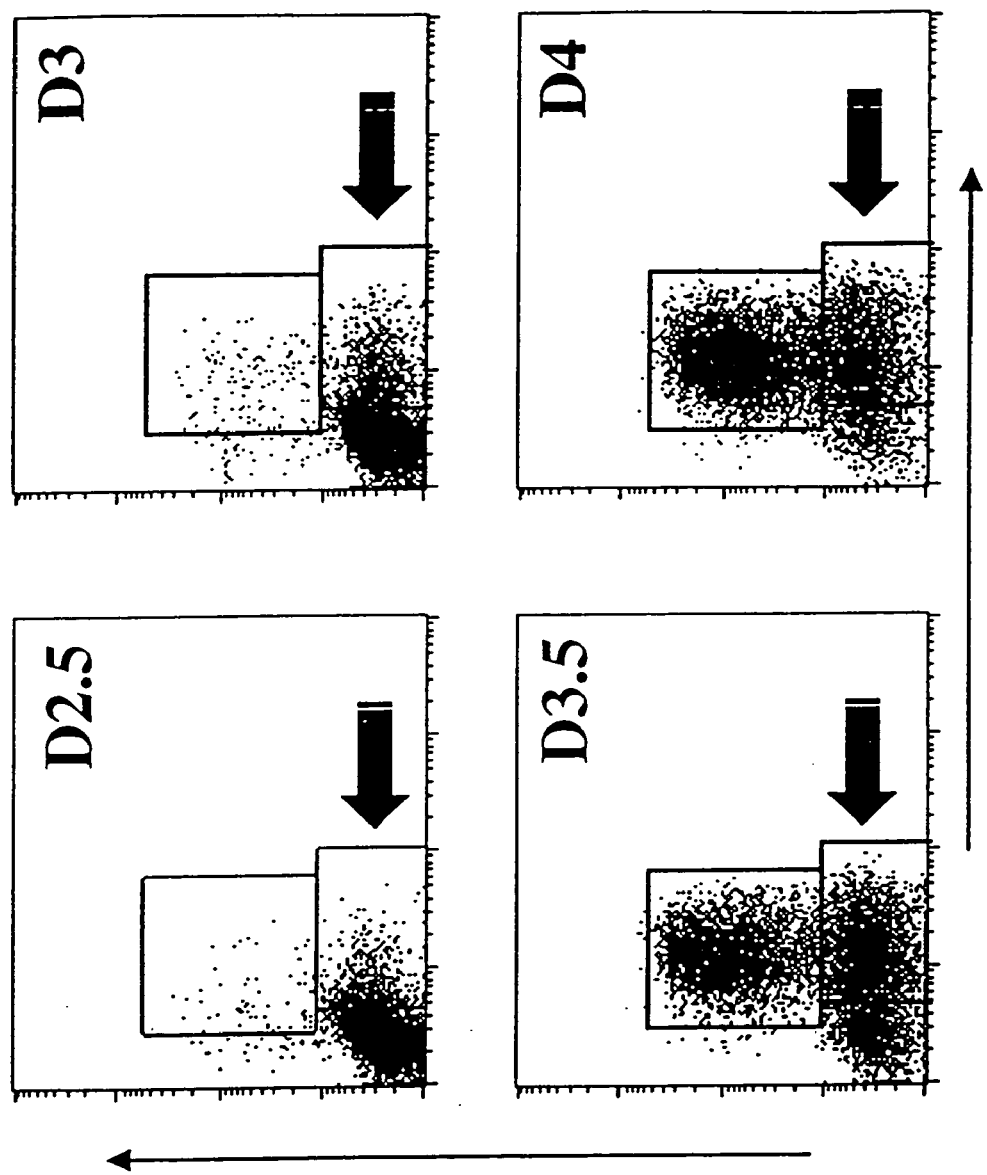
FIG. 18 depicts the kinetics of expression of GFP (brachyury) and Flk-1 in EBs differentiated for 2.5, 3.0, 3.5 and 4.0 days. Arrows indicate the GFP$^+$ population isolated used for the analyses in subsequent studies.
Figure 19:
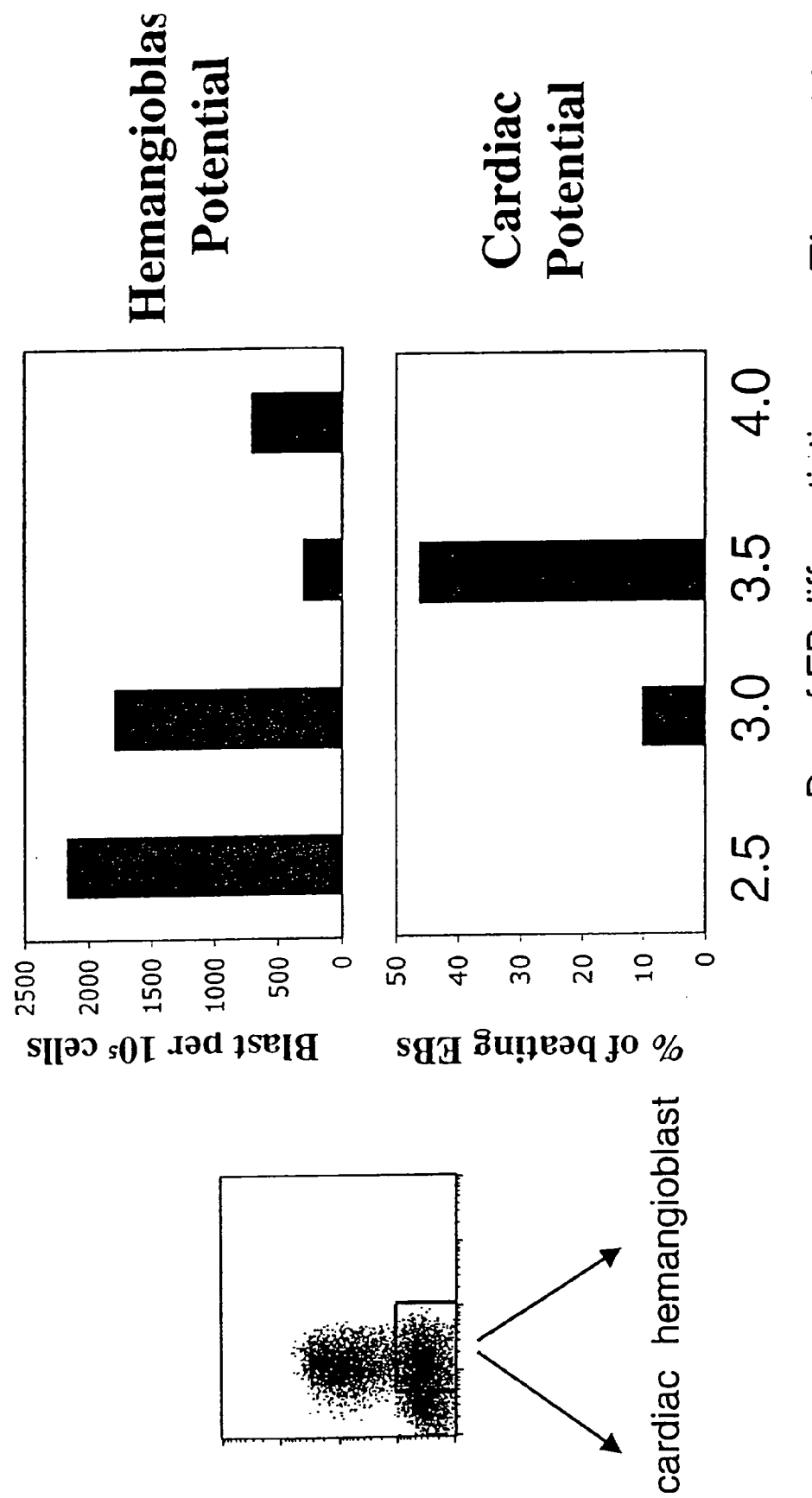
FIG. 19 depicts the hemangioblast and cardiac potential of the GFP$^+$ populations isolated from the four stages of EB differentiation. Cells from each stage were isolated by cell sorting, reaggregated for 24 hours and analyzed for hematopoietic and cardiac potential. Data are indicated as blast colonies (hemangioblast) per 1×10$^5$ cells recovered from the reaggregation culture or as the % of aggregates that gave rise to beating cell masses indicative of cardiac muscle differentiation.
Figure 20:
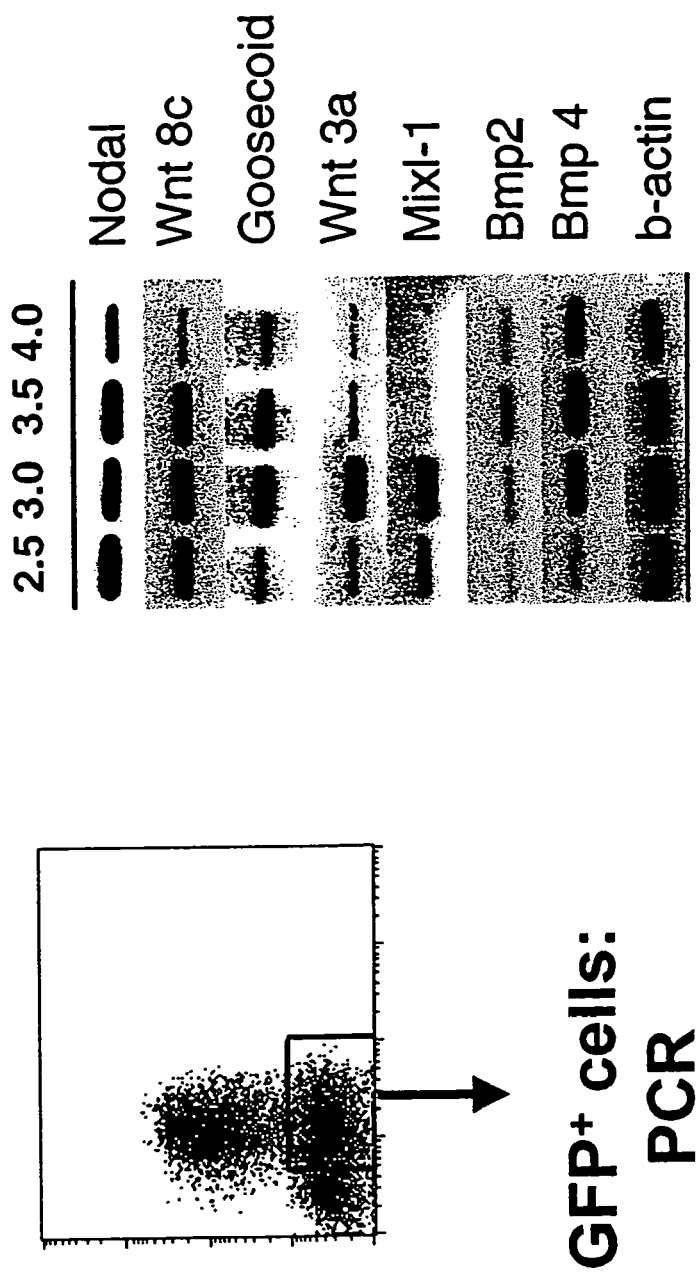
FIG. 20 provides the RT-PCR expression analysis of the indicated genes in the four GFP$^+$ EB-derived cells populations. Numbers indicate day of EB differentiation.

The preliminary kinetic analysis described in Example 6 demonstrated that subpopulations of mesoderm with distinct developmental fates were generated in a defined temporal fashion. A more detailed kinetic analysis showed the dynamic development of the GFP⁺ Flk1⁻ (hereafter referred to as the GFP⁺ population) population between days 2.5 and 4.0 of differentiation (FIG. 18). When isolated and reaggregated, the day 2.5 and 3.0 GFP⁺ fractions generated blast cell colonies (indicated as hemangioblast potential in FIG. 19) that represent the earliest stages of hematopoietic and endothelial commitment (FIG. 19). This population of GFP⁺ cells displayed little cardiomyocyte (cardiac) potential. In contrast to the early GFP⁺ cells, those isolated from day 3.5 EBs showed significantly reduced BL-CFC potential, but were efficient at differentiating into cardiomyocytes. GFP⁺ cells isolated from day 4 EBs did not give rise to cardiomyoctes and had little capacity to generate BL-CFC, suggesting they may be fated to some other mesodermal lineage. Gene expression analysis supported these functional assays and demonstrated molecular differences between the four GFP⁺ fractions (FIG. 20). While some genes were expressed in all populations, others showed intriguing differential patterns. Wnt3a, a gene thought to be important for hematopoietic development and inhibitory for cardiac differentiation, was expressed in the day 2.5 and 3.0 populations and down regulated in the day 3.5 and 4.0 cells. This pattern is consistent with the change in developmental potential of these populations from hematopoietic/vascular to cardiac muscle. A second pattern of interest is that of the gene Mixl-1. This gene, which plays a role in the development of mesoderm and endoderm, was expressed in the day 2.5 and 3.0 GFP populations but not in the day 3.5 and 4.0 fractions. Taken together, the findings of this example clearly demonstrate that mesoderm populations with different developmental potential are generated in a defined temporal pattern within the EBs. In addition, expression analysis of the mesoderm/endoderm gene Mixl-1 indicates that cells with endoderm potential are also generated at a specific time, namely between day 2.5 and 3.0 of differentiation.

Figure 21:
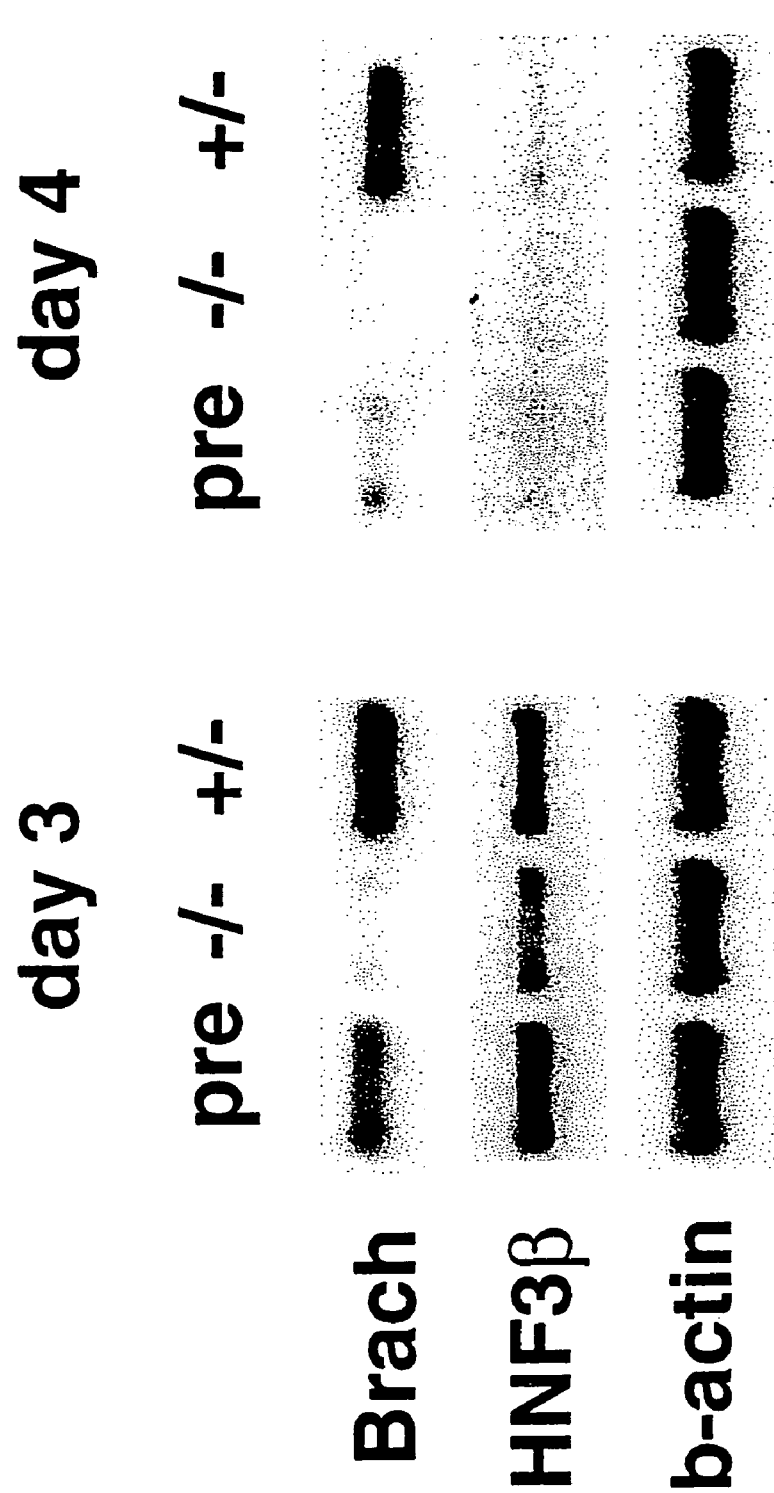
FIG. 21 shows HNF3 β expression in GFP$^+$ populations isolated from day 3.0 and 4.0 EBs. Pre represents cells prior to sorting, –/– are cells that express no GFP or Flk-1 and +/– represents the GFP$^+$ Flk-1$^-$-population.

To further investigate the kinetics of endoderm development, GFP⁺ cells from day 3.0 and 4.0 EBs were isolated and cultured under conditions that promote the differentiation into hepatocyte-like cells. As shown in FIG. 21, GFP⁺ cells (+/−) isolated from day 3.0 but not those from day 4.0 displayed endoderm potential as defined by expression of HNF3β. These findings indicate that endoderm is generated within the GFP⁺ population at a specific period of time, prior to day 4 of differentiation.

EXAMPLE 11

Developmental Potential of GFP⁺ populations In Vivo

To further evaluate the endoderm potential of the GFP⁺ population, GFP⁺ and GFP⁻ day 2.5 EB cells were cultured for 14 day days under conditions known to promote hepatocyte differentiation and then transplanted under the kidney capsule of recipient SCID-beige mice. Several mice were sacrificed immediately following the transplant, the kidney with the graft was sectioned and the sections were stained with antibodies against Hep1 and AFP. Hep1 is a specific marker of hepatocytes whereas AFP is expressed in definitive endoderm and immature cells of the hepatocyte lineage. Some of the cells within the section stained positive for Hep1, whereas other cells, in the vicinity of the Hep1⁺ cells were found to express AFP. No Hep1⁺ or AFP⁺ cells were found in the graft of the GFP negative cells. These findings support PCR data and demonstrate that there culture conditions support the development of cells with characteristics of immature hepatocytes, as defined by express of Hep1.

While these transplantation experiments demonstrate the presence of hepatocyte-like cells in the grafts immediately following transplantation, it was difficult to monitor the maturation of these populations over time, as the transplanted tissues generated tumor-like masses known as teratomas. The teratomas likely develop from contaminating undifferentiated ES cells or from GFP⁺ primordial germ cells that are known to be of mesoderm origin and to express brachyury.

EXAMPLE 12

Induction of Mesoderm and Endoderm by Activin

Figure 22:
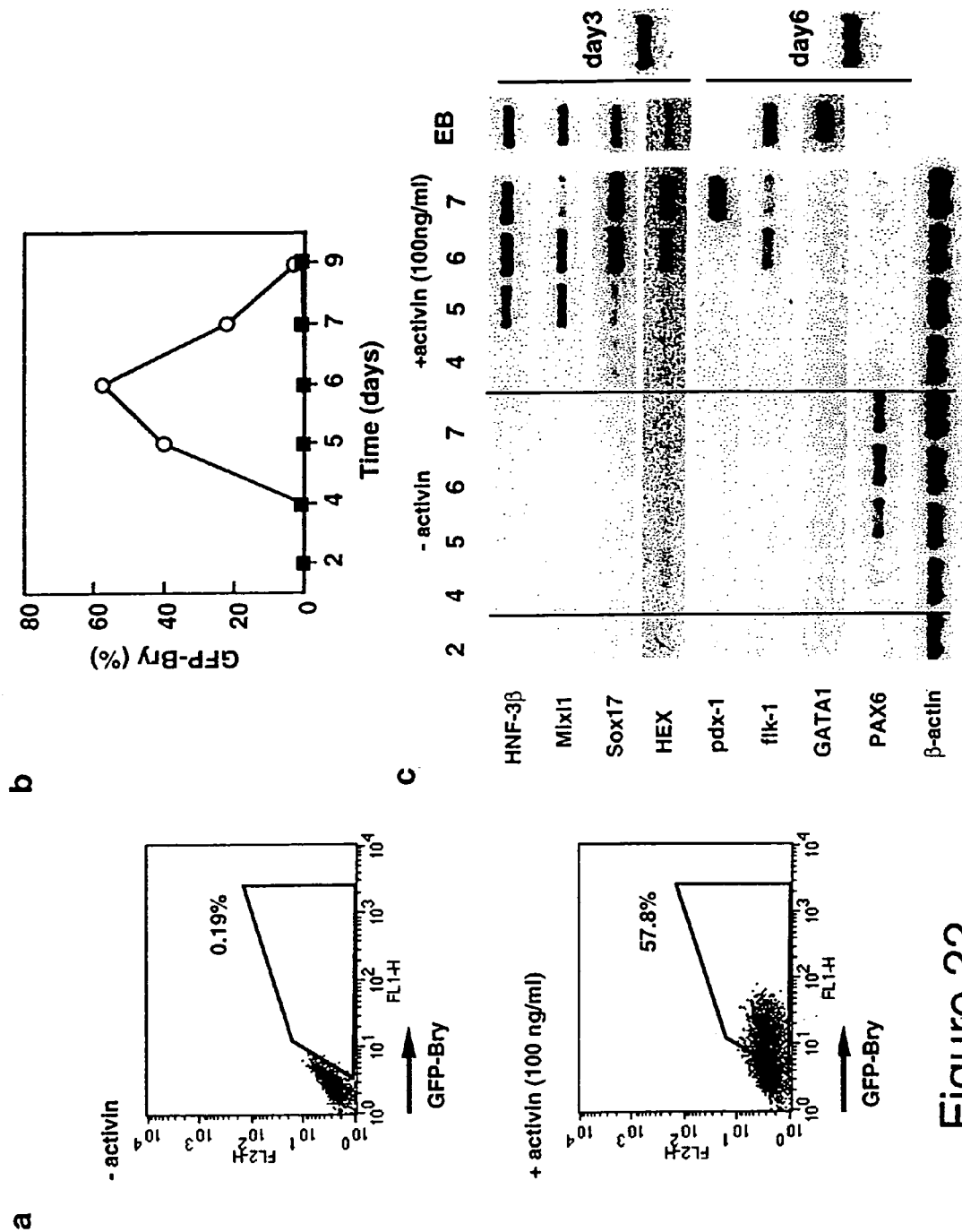
FIGS. 22A-C demonstrate the effects of activin on development of EBs in serum-free cultures. A) FACS profile showing GFP expression in day 6 EBs differentiated in the presence of 100 ng/ml of activin. B) Kinetics of GFP induction in cultures containing 100 ng/ml of activin. Open circles are EB differentiated in the presence of activin, closed squares are EBs differentiated in absence of activin. C) RT-PCR expression analysis of indicated genes in day 6 EBs grown in the presence (+activin) or absence (–activin) of activin. Numbers indicate day of EB differentiation.

To further enrich for cells with endodermal potential, the effects of growth factors known to induce this cell population in other model systems were tested. Studies in Xenopus have shown that activin will induce both mesoderm and endoderm from ectoderm in culture. Of particular interest was the observation that activin behaved as a morphogen in this model in that it induced different cell types at different concentrations used. To determine if activin displayed similar potential in the ES/EB system, it was added to the EB cultures using the following protocol. ES cells were differentiated for 2 days in Stem Pro 34 medium without serum. At this stage, the developing EBs were harvested and recultured in IMDM supplemented with serum replacement (serum free) and activin at a concentration of 100 ng/ml. EBs were harvested at different days and assayed for GFP⁺ expression and expression of genes indicative of ectoderm, mesoderm and endoderm development. As shown in FIG. 22A,B this amount of activin-induced brachyury as measured by GFP. While the kinetics of GFP induction was delayed compared to EBs differentiated in serum, this concentration of activin did induce substantial numbers of brachyury positive cells (60%) by day 6 of differentiation. Molecular analysis indicated that the activin-induced cells expressed a broad spectrum of genes associated with endoderm development including HNF3β, Mixl-1, Sox17, Hex-1, and pdx-1 (FIG. 23C). Induction of pdx-1 is of interest, as this gene is essential for pancreas development. Genes associated with hematopoietic development, such as GATA-1 and those indicative of neuroectoderm differentiation such as PAX6 were not induced by activin.

To determine if activin displayed morphogenic properties in the ES differentiation model, different concentrations of the factor were added to the EB cultures. As little as 1 ng/ml of activin induced GFP⁺ expression (10% of the total population) by 7 days of culture (FIG. 23A). The frequency of GFP⁺ cells increased to 40% in cultures stimulated with 3 ng/ml and reached plateau levels of greater than 50% at 30 ng/ml. Gene expression analysis of these populations indicated that different concentrations of activin did induce different developmental programs. EB differentiated in the presence of 1 or 3 ng/ml of activin showed weak, if any, expression of the genes indicative of endoderm development (FIG. 23A). HNF3β, Sox17, Hex-1 were all induced in cultures stimulated with 10, 30, or 100 ng/ml of activin. Pdx-1 expression required the highest amount of activin and was induced best in EBs stimulated with 100 ng/ml. Neither GATA1 nor c-fms was expressed at any concentration of activin. The pattern of PAX6 expression was the reverse to that of the endoderm genes and was downregulated with increasing concentrations of activin.

Figure 24:
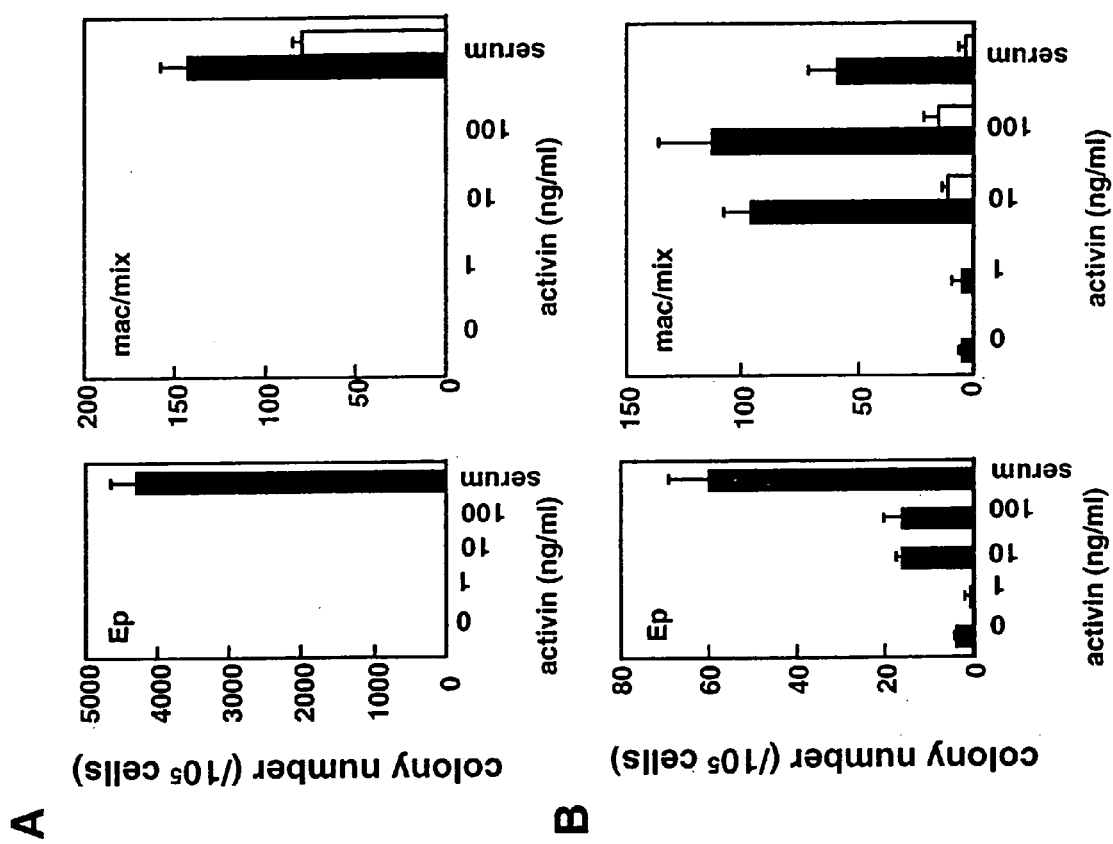
FIGS. 24A and B show the hematopoietic progenitor content of EBs differentiated in the presence of different concentrations of activin. A) Progenitor potential of day 7 EBs, Ep are primitive erythroid progenitors, mac/mix represent definitive hematopoietic progenitors. B) Progenitor potential of day 7 activin-induced EBs following 2.5 days of exposure to serum.

Activin-induced EBs did not express genes associated with hematopoietic commitment indicating that this developmental program was not induced. To further evaluate the hematopoietic potential of these EBs, they were analyzed for progenitor potential. As expected from the molecular analysis, these EBs contained no appreciable numbers of primitive (Ep) or definitive (mac/mix) hematopoietic progenitors (FIG. 24A). When these activin induced EBs were further stimulated with serum for 2.5 days, however, they did generate some hematopoietic progenitors, indicating that they do contain mesodermal potential (FIG. 24B).

PCR analysis demonstrated that activin induced expression HNF3β as well as other genes known to be involved in endoderm differentiation. To better estimate the proportion of endodermal progenitors in the activin-induced EBs, cells from cultures stimulated with 100 ng/ml activin were stained with antibodies against HNF3β and Hex1. EBs from un-induced cultures were used as controls (Activin−). A significant portion of the activin induced population (estimated at 50-60% of total) expressed both HNF3β and Hex1. None of the cells in the un-induced EBs expressed these proteins. These findings clearly demonstrate that a substantial number of cells within these EBs are of the endoderm lineage.

Figure 25:
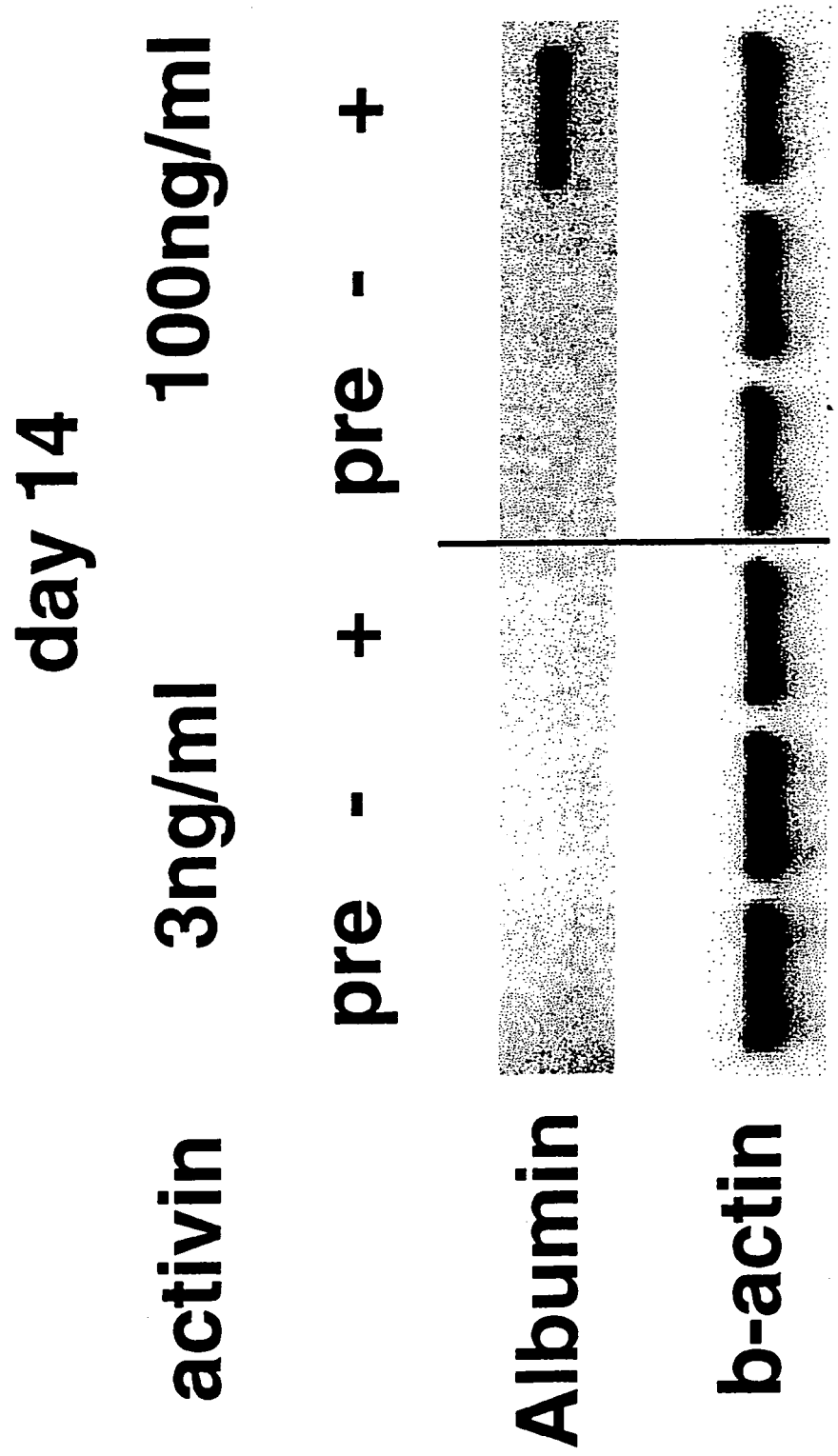
FIG. 25 shows the development of albumin expressing cells from GFP$^+$ cells induced with ether 3 or 100 ng/ml of activin. GFP$^+$ and GFP$^-$ cells were isolated at day 6 of differentiation and cultured for a further 8 days in the conditions previously described to support hepatocyte differentiation.

To further investigate the potential of these activin-induced populations, GFP+cells were isolated from EBs stimulated with 3 ng or 100 ng and cultured further (14 day total) in hepatocyte conductions. As shown in FIG. 25, only cells from the 100 ng cultures differentiated into cells that expressed albumin consistent with liver differentiation. Taken together, the findings from these studies indicate that activin functions as a morphogen in the ES/EB system and that high concentration are required for endoderm induction.

Figure 26A:
FIGS. 26A and B depict three-week old renal grafts of bry$^+$ (FIG. 26A) and bry$^-$ (FIG. 26B) cell populations.
Figure 26B:
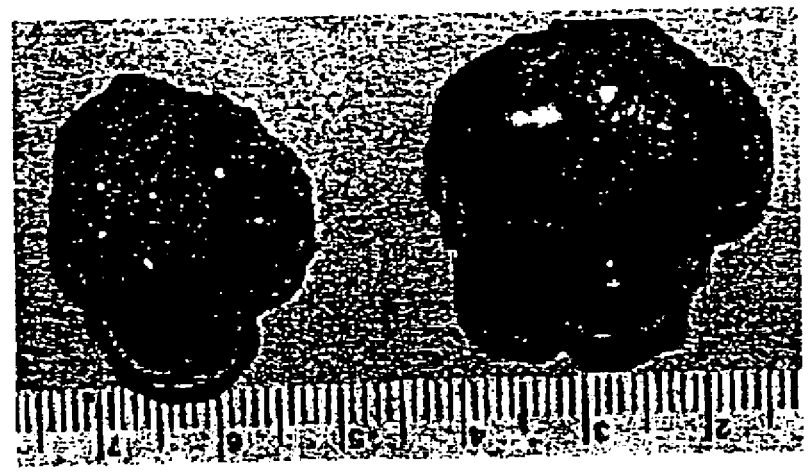
FIG. 26C depicts sections of grafts of the bry$^+$ and bry$^-$ populations.

If the teratomas generated by the serum-induced brachyury$^+$ cells resulted from the presence of primordial germ cells, it is possible that the activin induced cells may represent a better source of progenitors for transplantation, as the germ-cell program may not be induced under these conditions. To test this hypothesis, GFP$^+$ and GFP$^-$ cells were isolated from EBs induced with 100 ng/ml of activin and cultured for 14 days to promote the differentiation of hepatocyte-like cells. Following this culture period, the cells were harvested and transplanted to the kidney capsule of recipient animals. Three weeks following transplantation, the mice were sacrificed and the kidneys analyzed. Results are shown in FIGS. 26A-C. All mice engrafted with GFP$^-$ cells developed large, multilineage teratomas, consisting of cells from all three germ layers. In contrast, no teratomas were detected in the animals transplanted with GFP$^+$ cells. These cells give rise to differentiated cell masses consisting of endodermal and mesodermal derived tissues including gut epithelium, bone and skeletal muscle. In some instances, skin was also observed in the graft from the GFP$^+$ cells, suggesting that this lineage might also develop from a bry$^+$ cell. These findings indicate that it is possible to generate GFP$^+$ populations from a bry$^+$ cell. These findings indicate that it is possible to generate GFP$^+$ populations that give rise to differentiated tissue without forming teratomas following transplantation.

EXAMPLE 13

Developmental Potential of bry$^+$/c-kit$^-$ and bry$^+$/c-kit$^+$ Cells

Figure 27A:
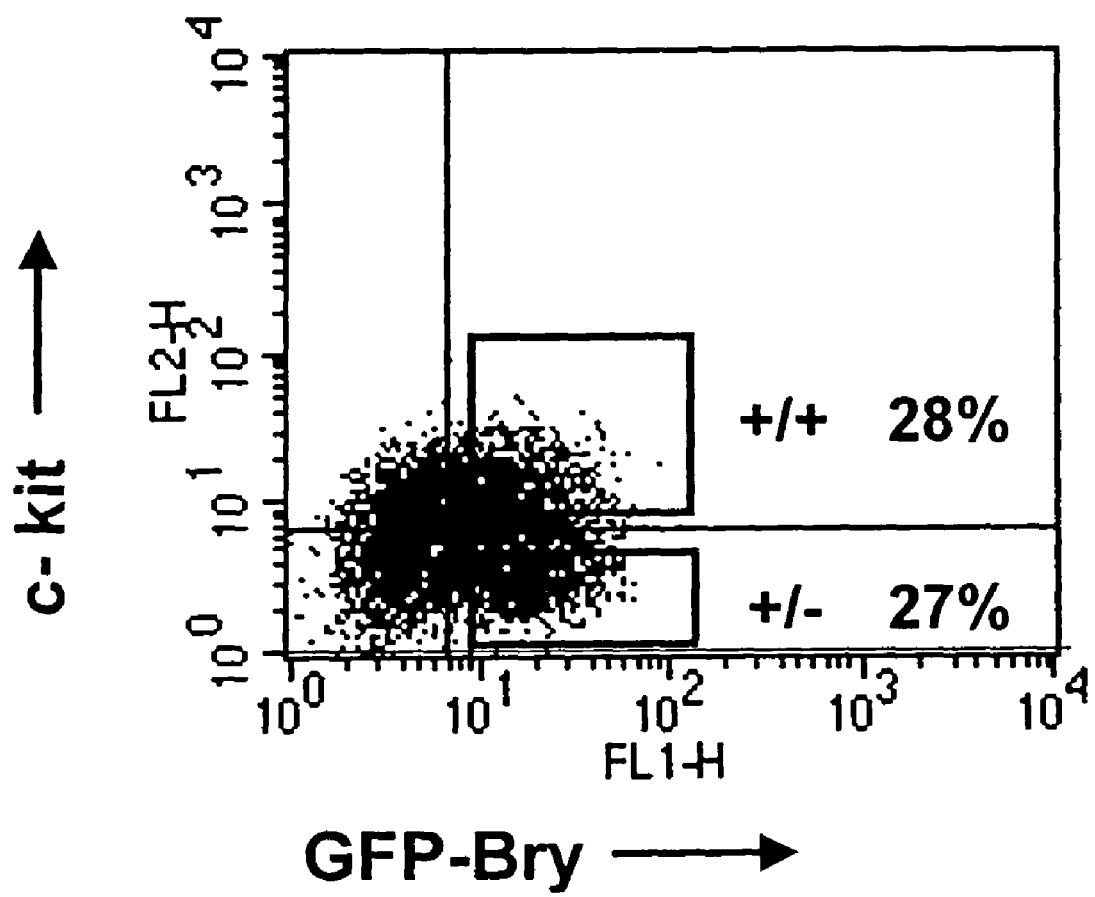
FIG. 27A is a FACS profile indicating the bry$^+$/c-kit$^+$ (+/+) and bry$^+$/c-kit$^-$ (+/–) fractions isolated from day three serum-stimulated EBs. Numbers represent the proportion of cells in each of the fractions.
Figure 27B:
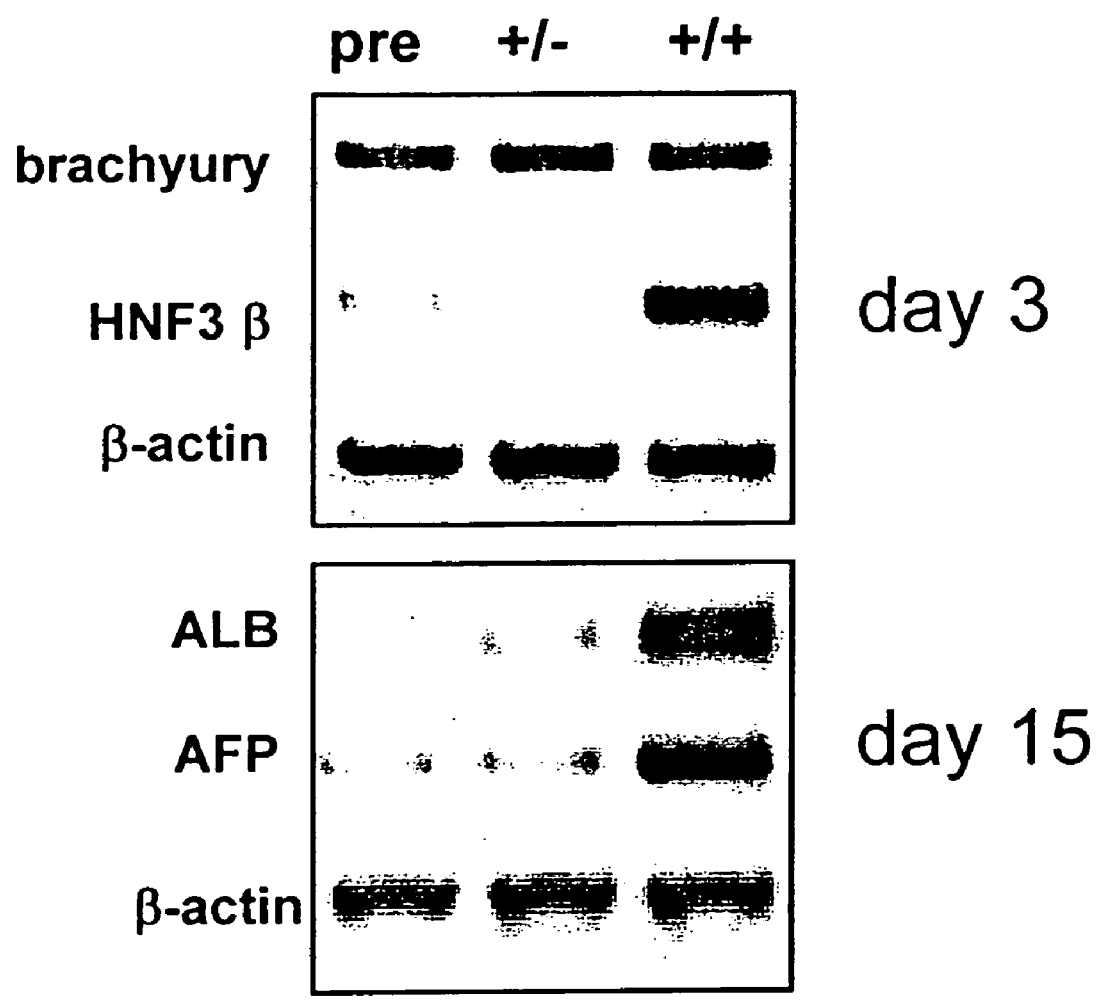
FIG. 27B shows expression analysis of each of the fractions. Day 3 represents cells analyzed immediately following sorting. Day 15 represents cell populations cultured for 15 days in hepatocyte conditions.

The foregoing examples clearly indicate that the hepatocyte lineage develops from a bry$^+$ cell population that has both mesoderm and endoderm potential. Analysis of the bry$^+$ fraction revealed that a subpopulation of these cells expressed the receptor tyrosine kinase c-kit (FIG. 27A) and that this population was distinct from those cells that expressed Flk-1. To determine if c-kit expression could be a useful marker for the segregation of cell with endodermal potential, bry$^+$/c-kit$^-$ (+/−) and bry$^+$/c-kit$^+$ (+/+) cells from day 3 serum-stimulated EBs were assayed for hepatocyte potential. As shown in FIG. 27B, HNF3β, AFP and ALB expressing cells were all derived from bry$^+$/c-kit$^+$ population. To estimate the endodermal potential of this fraction, sorted cells were plated onto glass coverslips and stained with an antibody to HNF3β. Greater than 80% of the bry$^+$/c-kit$^+$ cells expressed HNF3β protein, whereas less than 10% bry$^+$/c-kit$^-$ were positive. These findings indicate that endodermal progenitors express both brachyury and c-kit and that this population is highly enriched for cells with endodermal potential. Isolation of cells based on brachyury and c-kit expression provides a novel strategy for the isolation of endodermal progenitors.

EXAMPLE 14

Developmental Potential of Activin-induced Cells

Figure 23:
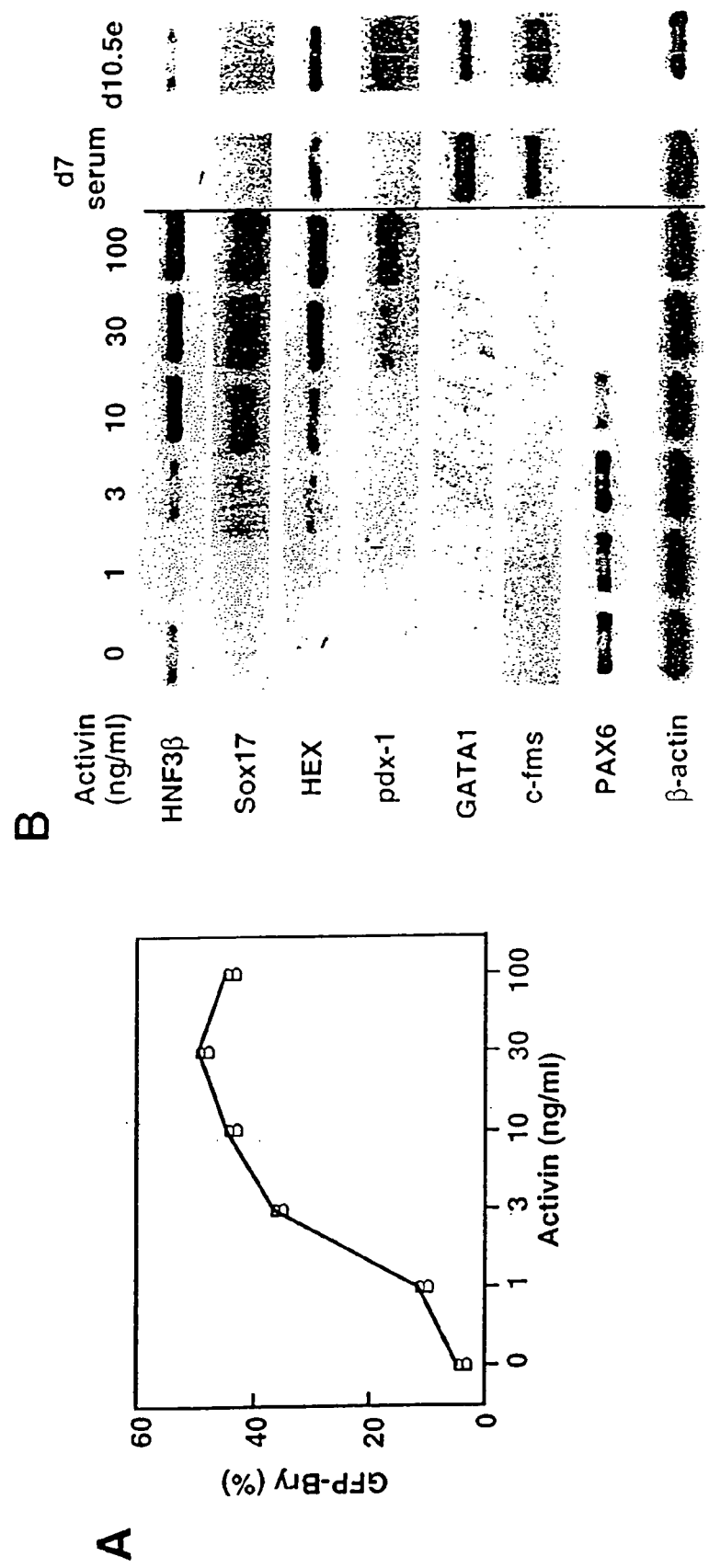
FIGS. 23A and B show the effects of different concentrations of activin on the developmental potential of EBs. A) GFP expression in day 7 EBs induced with different concentrations of activin. B) RT-PCR expression analysis of day 7 EBs induced with different concentrations of activin.

The PCR analysis presented in FIG. 23 indicates that different concentrations of activin induce different developmental programs and that cells with endodermal potential are induced with the highest levels of this factor. To quantify the differential response of activin, cells stimulated with different concentrations of activin were adhered to coverslips and stained with the anti-HNF3β antibody. More than 50% of the entire EB population stimulated with 100 ng/ml of activin expressed HNF3β whereas only 10% of the cells stimulated with 3 ng/ml were positive. Only background levels of staining were observed in the non-stimulated population. These findings demonstrate that high concentrations of activin can stimulate a robust endodermal program, representing a significant portion of entire EB population.

Figure 28:
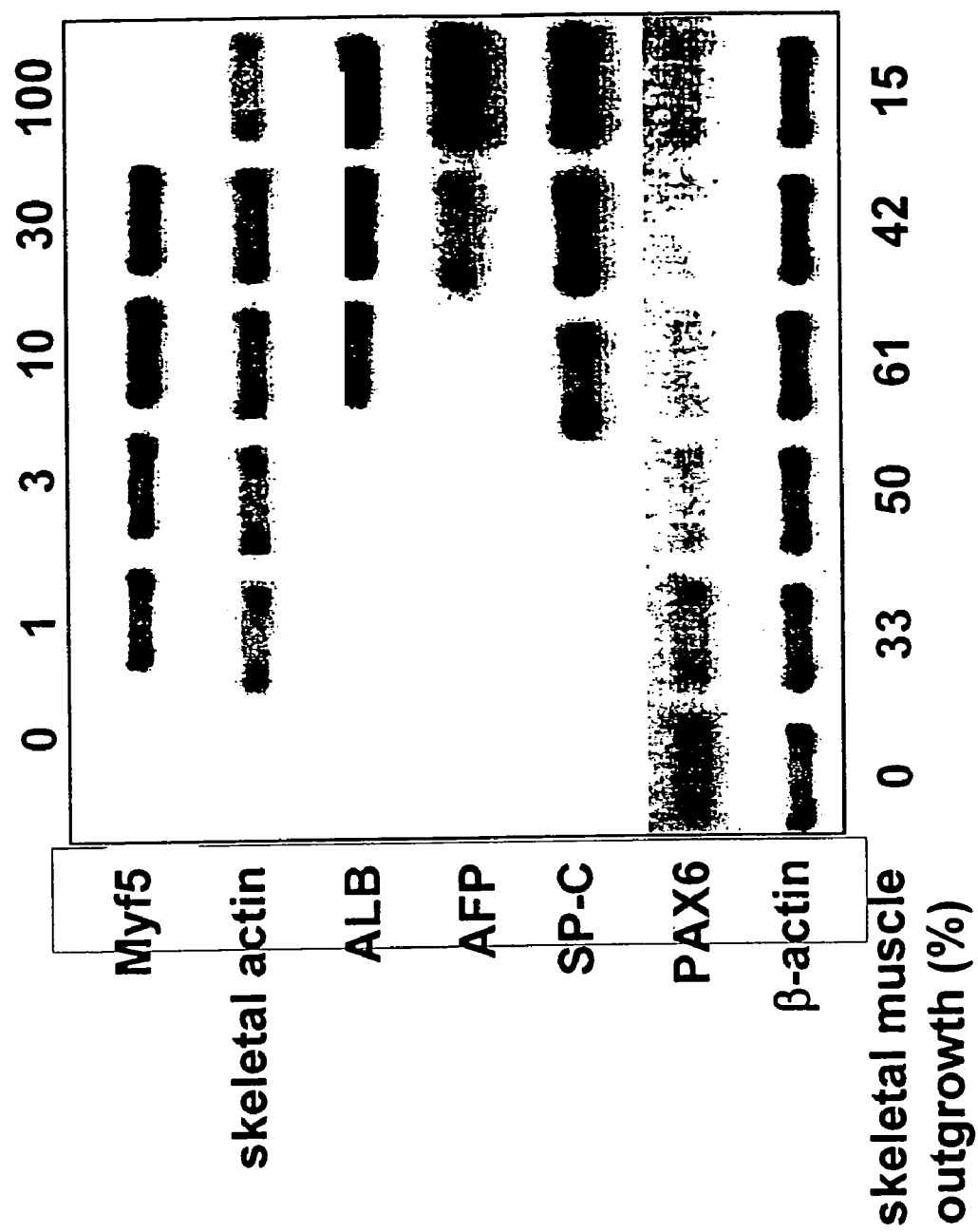
FIG. 28 depicts expression analysis of cell populations derived from EBs induced with different concentrations of activin. Numbers at the top of the figure indicate activin concentration. Numbers at the bottom of the figure represent an estimate of the proportion of EBs with skeletal muscle outgrowths.

As a further assessment of the potential of activin treated cells, day 6 EBs differentiated in the presence of different concentrations of this factor were transferred to serum replacement media for 4 days and then replated in hepatocyte conditions for an additional 4 days. At day 14 of culture, the cells from each group were harvested and subjected to PCR expression analysis. Expression of Myf5 and skeletal actin were monitored to evaluate skeletal muscle development representing an additional mesoderm-derived lineage. Surfactant protein C(SP-C), a lung-specific gene, was included as a marker of endoderm differentiation in addition to AFP and ALB. As shown in FIG. 28, Myf5 and skeletal actin were expressed in cultures stimulated with as little as 1 ng/ml of activin and this expression was detected over a broad range of factor concentrations. Expression of both genes was, however, downregulated at the highest concentration of activin (100 ng/ml). Cultures stimulated with low amounts of activin contained groups of cells with the morphology of skeletal muscle. Immunostaining demonstrated that these cells expressed both skeletal myosin and α-actinin, indicating that they are of the skeletal muscle lineage. Evaluation of the proportion of replated EBs that generated skeletal muscle outgrowths was consistent with the gene expression analysis, as those stimulated with 3 and 10 ng/ml displayed the most robust skeletal muscle development as depicted in FIG. 28. The expression patterns of the three endodermal genes differed from that observed for the skeletal muscle genes. None were expressed at low activin concentrations and all were readily detected in cultures stimulated with the highest concentrations of the factor. Expression of PAX6 was restricted to untreated cultures and those stimulated with low concentrations of factor. The findings from this analysis confirm and extend those from Example 12 hereinabove in demonstrating that different concentrations of activin induce different developmental programs, with low concentration favoring a mesodermal fate and high concentrations an endoderm fate. In addition, these results indicate that the endodermal cells induced by activin are able to differentiate and give rise to cells with hepatocyte and lung characteristics.

Brachyury positive and negative populations isolated from EBs stimulated with low and high concentrations of factor were also analyzed for expression of the skeletal muscle and endoderm genes. As shown in FIG. 29, both myf5 and skeletal actin expression were restricted to the population generated from the bry+ population isolated from EBs stimulated with 3 ng/ml of activin. Similarly, the endoderm genes were expressed in the brachyury+-derived cells isolated from EBs generated in the presence of 100 ng/ml of factor. These findings further demonstrate that both mesoderm and endoderm develop from brachyury+ cells.

The invention claimed is:

1. A method of generating a cell population enriched for endoderm cells comprising culturing mammalian embryoid bodies in the presence of a concentration of activin of at least 30 ng/ml, whereby said embryoid bodies differentiate to generate a cell population enriched for endoderm.

2. The method of claim 1 further comprising isolating endoderm cells wherein said endoderm cells express at least one of HNF3β, Mixl-1, Sox17, Hex-1 and pdx-1.

3. The method of claim 1 wherein the concentration of activin is from 30 ng/ml to about 100 ng/ml.

4. The method of claim 1 wherein the concentration of activin is about 100 ng/ml.

5. The method of claim 1 further comprising culturing the embryoid bodies in the absence of serum.

6. The method of claim 1 wherein the embryoid bodies are human embryoid bodies.

7. The method of claim 1 wherein the embryoid bodies are human embryoid bodies and the concentration of activin is about 100 ng/ml.

* * * * *

UNITED STATES PATENT AND TRADEMARK OFFICE
CERTIFICATE OF CORRECTION

PATENT NO. : 7,763,466 B2
APPLICATION NO. : 10/514759
DATED : July 27, 2010
INVENTOR(S) : Gordon M. Keller et al.

It is certified that error appears in the above-identified patent and that said Letters Patent is hereby corrected as shown below:

At column 1, line 19, please replace "may have" with --has--.

Signed and Sealed this

Ninth Day of November, 2010

David J. Kappos
*Director of the United States Patent and Trademark Office*